United States Patent
Willuda et al.

(10) Patent No.: US 12,221,479 B2
(45) Date of Patent: Feb. 11, 2025

(54) PHARMACEUTICAL COMBINATION OF ANTI CEACAM6 AND TIM3 ANTIBODIES

(71) Applicants: Bayer Aktiengesellschaft, Leverkusen (DE); Deutsches Krebsforschungszentrum, Heidelberg (DE)

(72) Inventors: Jörg Willuda, Glienicke/Nordbahn (DE); Mark Trautwein, Wülfrath (DE); Rienk Offringa, Heidelberg (DE); Hans-Henning Böhm, Heidelberg (DE); Philipp Beckhove, Heidelberg (DE)

(73) Assignees: Bayer Aktiengesellschaft, Leverkusen (DE); Deutsches Krebsforschungszentrum, Heidelberg (DE)

(*) Notice: Subject to any disclaimer, the term of this patent is extended or adjusted under 35 U.S.C. 154(b) by 815 days.

(21) Appl. No.: 17/416,958

(22) PCT Filed: Dec. 12, 2019

(86) PCT No.: PCT/EP2019/084849
§ 371 (c)(1),
(2) Date: Jun. 21, 2021

(87) PCT Pub. No.: WO2020/126808
PCT Pub. Date: Jun. 25, 2020

(65) Prior Publication Data
US 2022/0089721 A1 Mar. 24, 2022

(30) Foreign Application Priority Data
Dec. 19, 2018 (EP) ..................... 18214059

(51) Int. Cl.
*A61K 39/395* (2006.01)
*A61K 45/06* (2006.01)
*A61P 35/00* (2006.01)
*C07K 16/28* (2006.01)

(52) U.S. Cl.
CPC ...... *C07K 16/2803* (2013.01); *A61K 39/3955* (2013.01); *A61K 45/06* (2013.01); *A61P 35/00* (2018.01); *C07K 2317/51* (2013.01); *C07K 2317/515* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 7,943,743 B2 | 5/2011 | Korman | |
| 8,008,449 B2 | 8/2011 | Korman | |
| 8,217,149 B2 | 7/2012 | Irving | |
| 8,609,089 B2 | 12/2013 | Langermann | |
| 8,779,108 B2 | 7/2014 | Queva | |
| 8,900,587 B2 | 12/2014 | Carven | |
| 2011/0212095 A1 | 9/2011 | Song | |
| 2014/0341917 A1 | 11/2014 | Nastri | |
| 2014/0356353 A1 | 12/2014 | Queva | |
| 2015/0079109 A1 | 3/2015 | Li | |
| 2017/0275375 A1 | 9/2017 | Rossi | |

FOREIGN PATENT DOCUMENTS

| | | |
|---|---|---|
| CN | 102482701 A | 5/2012 |
| EP | 3560957 A2 | 10/2019 |
| WO | 2011034660 A1 | 3/2011 |
| WO | 2012040824 A1 | 4/2012 |
| WO | 2013173223 A1 | 11/2013 |
| WO | 2014163684 A1 | 10/2014 |
| WO | 2015117002 A1 | 8/2015 |
| WO | 2015126548 A1 | 8/2015 |
| WO | 2016150899 A2 | 9/2016 |
| WO | 2016161270 A1 | 10/2016 |
| WO | 2017178493 A1 | 10/2017 |
| WO | 2017205721 A1 | 11/2017 |
| WO | 2017210058 A1 | 12/2017 |
| WO | 2018013818 A2 | 1/2018 |
| WO | 2018039020 A1 | 3/2018 |
| WO | 2018088877 A2 | 5/2018 |
| WO | 2018129553 A1 | 7/2018 |
| WO | 2020099230 A1 | 5/2020 |

OTHER PUBLICATIONS

Zhao et al. (2024). Discover Oncology. 15(1):186 (9 pages).*
Cheng et al. (2012). Eur. J. Cancer. 50(4):713-721.*
Russian Office Action, Federal Service for Intellectual Property, Russian Patent Application No. 2021121091, Apr. 18, 2023, pages.
Sabeeh-Ur-Rehman, B et al., Role of immunotherapy in bladder cancer: past, present and future, Cancer Chemotherapy and Pharmacology, Jan. 24, 2018, vol. 81, pp. 629-645.
Tang et al., What is synergy? The Saariselkä agreement revisited. Front Pharmacol. 2015, vol. 6, No. 181, pp. 1-5.
Tallarida, R.J., Drug synergism: its detection and applications, J Pharmacol Exp Ther. 2001, vol. 298, No. 3, pp. 865-872.
Tol et al., Chemotherapy, bevacizumab, and cetuximab in metastatic colorectal cancer, N Engl J Med 2009, vol. 360, pp. 563-572.
Johnson et al. Emerging Role and Targeting of Carcinoembryonic Antigen-related Cell Adhesion Molecule 6 (CEACAM6) in Human Malignancies, Clinical Cancer Drugs, 2015, vol. 2, No. 2, pp. 100-111.
Akashi, K., TIM-3 is a Novel Therapeutic Target for Eradicating Acute Myelogenous Leukemia Stem Cells, In: Nakao K, Minato N, Uemoto S. editors, Innovative Medicine: Basic Research and Development, 2015, pp. 307-315.

(Continued)

*Primary Examiner* — Christine J Saoud
*Assistant Examiner* — Jon M Lockard
(74) *Attorney, Agent, or Firm* — Taft Stettinius & Hollister LLP

(57) ABSTRACT

The present disclosure relates to combinations of at least two components, component A and component B, component A being anti-CEACAM6 antibody TPP-3310 and component B being an anti-TIM-3 antibody, preferentially cobolimab, MBG-453, BMS-986258, Sym-023, LY-3321367 or INCAGN-2390.

11 Claims, No Drawings
Specification includes a Sequence Listing.

(56) References Cited

OTHER PUBLICATIONS

Manchado et al., A combinatorial strategy for treating KRAS mutant lung cancer, Nature, 2016, vol. 534, pp. 1-41.
Dermer G.B., Another Anniversary for the War on Cancer, Bio/Technology, 1994, vol. 12, p. 320.
Anonymous (Jan. 1, 2018) "History of Changes for study NCT03596372: Study of BAY1834942 in Patients With Solid Tumors", retrieved from URL:https://clinicaltrials.gov/ct2/history/NCT03596372?V6=View#StudyPageTop, pp. 1-6.
Balk-Moller, E. et al. (2014). "A Marker of Endocrine Receptor-Positive Cells, CEACAM6, is Shared by Two Major Classes of Breast Cancer," The American Journal of Pathology, 184(4):1198-1208.
Beauchemin (1999). "Redefined Nomenclature for Members of the Carcinoembryonic Antigen Family," Experimental Cell Research, 252:243-249.
Beauchemin, N. et al. (2013). "Carcinoembryonic antigen-related cell adhesion molecules (CEACAMs) in cancer progression and metastasis," Cancer Metastasis Rev., 32:643-671.
Beckhove, P. et al. (2004). "Specifically activated memory T cell subsets from cancer patients recognize and reject kenotransplanted autologous tumors," The Journal of Clinical Investigation, 114(1):67-76.
Blumenthal, R.D. et all. (2007). "Expression patterns of CEACAM5 and CEACAM6 in primary and metastatic cancers," BMC Cancer, 7(2):1-15.
Brand, F.X. et al. (2006). "Prospect for Anti-HER2 Receptor Therapy in Breast Cancer" Anticancer Res. 26:463-470.
Burugu, S. et al. (2018) "Emerging targets in cancer immunotherapy," Seminars in Cancer Biology, 52:39-52.
Butt, S. et al. (2018) "Role of immunotherapy in bladder cancer: past, present and future," Cancer Chemotherapy and Pharmacology, 18:629-645.
Cameron, S. et al. (2012). "Focal overexpression of CEACAM6 contributes to enhanced turmourigenesis in head and neck cancer via suppression of apoptosis," Molecular Cancer, 11(74):1-11.
Cavallaro, U. et al. (2004). "Cell Adhesion and Signalling by Cadherins and IG-CAMS in Cancer," Nature, 4:118-132.
Chan, C.H.F. et al. (2004). "Novel Mouse Model for Carcinoembryonic Antigen-Based Therapy," Molecular Therapy, 9 (6):775-785.
Cheng, T-M. et al. (2014). "Single domain antibody against carcinoembryonic antigen-related cell adhesion molecule 6 (CEACAM6) inhibits proliferation, migration, invasion and angiogenesis of pancreatic cancer cells," European Journal of Cancer, 50:713-721.
Choi, C. et al. (2005). "Enrichment of functional CD8 memory T cells specific for MUC1 in bone marrow of patients with multiple meyloma," Blood, 105(5):2132-2134.
Deng, X. et al. (2014). "Expression profiling of CEACAM6 associated with the tumorigenesis and progression in gastric adenocarcinoma," Genetics and Molecular Research, 13(3):7686-7697.
Du, X. et al. (2011). "Abstract 4582: Characterization of a new antibody that reacts with a tumor-specific variant of CEACAM-5 and CEACAM-6," Cancer Research, 71(8):1.
Duxbury, M.S. et al. (2004). "A Novel Role for Carcinoembryonic Antigen-Related Cell Adhesion Molecule 6 as a Determinant of Gemcitabine Chemoresistance in Pancreatic Adenocarcinoma Cells," Cancer Research, 64:3987-3993.
Duxbury, M.S. et al. (2005). "CEACAM6 is a Novel Biomarker in Pancreatic Adenocarcinoma and PanIN Lesions," 241 (3):491-496.
Duxbury, MS. et al. (2004). "CEACAM6 is a determinant of pancreatic adenocarcinoma cellular invasiveness," British Journal of Cancer, 91:1384-1390.
Feuerer, M. et al. (2001). "Therapy of human tumors in NOD/SCID mice with patient-derived reactivated memory T cells from bone marrow," Nature Medicine, 7(4):452-458.

Gemei, M. et al. (2013). "CD66c is a Novel Marker for Colorectal Cancer Stem Cell Isolation, and its Silencing Halts Tumor Growth in Vivo," Cancer, 729-738.
Gray-Owen, S. et al. (2006). "CEACAM1: contact-dependent control of immunity," Nature Reviews, 6:433-446.
Henick, B.S. et al. (2014). "The PD-1 pathway as a therapeutic target to overcome immune escape mechanisms in cancer," Expert Opin. Ther. Targets 18(12):1407-1420.
Hermeling, S. et al. (2004). "Structure-Immunogenicity Relationships of Therapeutic Proteins," Pharmaceutical Research, 21(6):897-903.
Horna, P. et al. (2007). "Cellular and Molecular Mechanisms of Tumor-Induced T-Cell Tolerance," Current Cancer Drug Targets, 7:41-53.
Horst, A.K. et al. (2004). "CEA-Related CAMs," HEP, 165:283-341.
International Preliminary Report on Patentability dated Sep. 26, 2017 for International Application No. PCT/EP2016/056104, filed Mar. 21, 2016, 10 pages.
International Search Report and Written Opinion dated Feb. 11, 2021 for International Application No. PCT/EP2019/084849, filed Dec. 12, 2019, 18 pages.
International Search Report and Written Opinion dated Jan. 15, 2020 for International Application No. PCT/EP2019/080520, 15 pages.
International Search Report and Written Opinion dated May 12, 2016 for International Application No. PCT/EP2016/056104, 15 pages.
Jager, E. et al. (2000). "Monitoring CD8 T cell responses to NY-ESO-1: Correlation of humoral and cellular immune responses," PNAS, 97(9):4760-4765.
Jantscheff, P. et al. (2003). "Expression of CEACAM6 in Resectable Colorectal Cancer: A Factor of Independent Prognostic Significance," Journal of Clinical Oncology, 21(19):3638-3646.
Kammerer, R. et al. (2010). "Coevolution of activating and inhibitory receptors within mammalian carcinoembryonic antigen families," BMC Biology, 8(12):1-21.
Khandelwal, N. et al. (2014). "Blockade of CEACAM-6 is required for breast tumor rejection in vivo," Cancer Research Institute, 68-69.
Kim, K. S. et al. (2013). "Overexpression and clinical significance of carcinoembryonic antigen-related cell adhesion molecule 6 in colorectal cancer," Clinica Chimica Acta, 415:12-19.
Kobayashi, M. et al. (2012). "Carcinoembryonic antigen-related cell adhesion molecules as surrogate markers for EGFR inhibitor sensitivity in human lung adenocarcinoma," British Journal of Cancer, 107:1745-1753.
Kolla, V. et al. (2009). "Carcinoembryonic cell adhesion molecule 6 in human lung: regulated expression of a multifunctional type II cell protein," Am J Physiol Lung Cell Mol Physiol 296:L1019-:1030.
Kuespert, K. et al. (2006). "CEACAMs: their role in physiology and pathophysiology," Current Opinion in Cell Biology, 18:565-571.
Kuroki, M. et al. (1992). "Three different NCA species, CGM6/CD67, NCA-95, and NCA-90, are comprised in the major 90 to 100-KDa band of granulocyte NCA detectable upon SDS-polyacrylamide gel electrophoresis," 182(2):501-506.
Latour, S. et al. (1997). "Regulation of T-Cell Antigen Receptor Signalling by Syk Tyrosine Protein Kinase," Molecular and Cellular Biology, 17(8):4434-4441.
Lee, O-J. et al. (2015). "CEACAM6 as detected by the AP11 antibody is a marker notable for mucin-producing adenocarcinomas," Virchows Arch, 466:151-159.
Letsch, A. et al. (2003). "Bone Marrow Contains Melanoma-reactive CD8+ Effector T Cells and, Compared with Peripheral Blood, Enriched Numbers of Melanoma-reactive CD8+ Memory T Cells," Cancer Research, 63:5582-5586.
Lewis-Wambi, J.S. et al. (2008). "Overexpression of CEACAM6 promotes migration and invasion of oestrogen-deprived breast cancer cells," European Journal of Cancer, 44:1770-1779.
Lin, J. et al. (Jan. 2001). "T Cell Receptor Signaling," Journal of Cell Science 114(Pt. 2):243-244.

(56) References Cited

OTHER PUBLICATIONS

Maraqa, L. et al. (2008). "Carcinoembryonic Antigen Cell Adhesion Molecule 6 Predicts Breast Cancer Recurrence following Adjuvant Tamoxifen," Clin Cancer Res, 14(2):405-411.
Marin-Acevedo, J.A. et al. (2018). "Next generation of immune checkpoint therapy in cancer: new developments and challenges," Journal of Hematology & Oncology, 11(39):1-20.
Niu, G. et al. (2012). "Molecular targeting of CEACAM6 using antibody probes of different sizes," Journal of Controlled Release, 161:18-24.
Obrink, B. (1997). "CEA adhesion molecules: multifunctional proteins with signal-regulatory properties," Current Opinion in Cell Biology, 9:616-626.
Ortenberg, R. et al. (2012). "Novel Immunotherapy for Malignant Melanoma with a Monoclonal Antibody That Blocks CEACAM1 Homophilic Interactions," Molecular Cancer Therapeutics, 11(6):1300-1310.
Pardoll, D.M. (2012). "Immunology beats cancer: a blueprint for successful translation," Nature Immunology, 13(12):1129-1132.
Pardoll, D.M. (Apr. 2012). "The Blockade of Immune Checkpoints in Cancer Immunotherapy," Nat. Rev. Cancer 12 (4): 252-264.
Poola, I. et al. (2006). "Expression of Carcinoembryonic Antigen Cell Adhesion Molecule 6 Oncoprotein in Atypical Ductal Hyperplastic Tissues is Associated with the Development of Invasive Breast Cancer," Cancer Prevention, 12 (15):4773-4783.
Riley, C.J. et al. (2009). "Design and Activity of a Murine and Humanized anti-CEACAM6 scFv in the Treatment of Pancreatic Cancer," Cancer Res. 69(5):1933-1940.
Romero, P. et al. (2006). "The Human T Cell Response to Melanoma Antigens," Advances in Immunology, 92:187-224.
Schmitz-Winnenthal, F.H. et al. (2005). "High Frequencies of Functional Tumor-Reactive T Cells in Bone Marrow and Blood of Pancreatic Cancer Patients," Cancer Res. 65(21):10079-10087.
Scholzel, S. et al. (2000). "Carcinoembryonic Antigen Family Members CEACAM6 and CEACAM7 are Differentially Expressed in Normal Tissues and Oppositely Deregulated in Hyperplastic Colorectal Polyps and Early Adenomas," American Journal of Pathology, 156(2):595-605.
Shen, X. et al. (2018) "Efficacy of PD-1 or PD-L1 inhibitors and PD-L1 expression status in cancer: meta-analysis," the BMJ, 9 pages.
Sommerfeldt, N. et al. (2006). "The Shaping of a Polyvalent and Highly Individual T-Cell Repertoire in the Bone Marrow of Breast Cancer Patients," Cancer Res. 66(16):8258-8265.
Strickland, L.A. et al.(2009). "Preclinical evaluation of carcinoembryonic cell adhesion molecule (CEACAM)6 as potential therapy target for pancreatic adenocarcinoma," Journal of Pathology, 218:380-390.
Strome et al. (2007). "A Mechanistic Perspective of Monoclonal Antibodies in Cancer Therapy Beyond Target-Related Effects" Oncologist 12:1084-1095.
Suntharalingam, G. et al. (Sep. 7, 2006). "Cytokine Storm in a Phase 1 Trial of the Anti-CD28 Monoclonal Antibody TGN1412," N Engl J Med 355(10):1018-1028.
Tsang, J.Y.S et al. (2013). "Expression and clinical significance of carcinoembryonic antigen-related cell adhesion molecule 6 in breast cancers," Breast Cancer Res Treat, 142:311-322.
Vermeer, A.W.P. et al. (Jan. 2000). "The Thermal Stability of Immunoglobulin: Unfolding and Aggregation of a Multi-Domain Protein," Biophysical Journal 78(1):394-404.
Voges, M. et al. (2012). "Extracellular Igc2 Constant Domains of CEACAMs Mediate PI3K Sensitivity during Uptake of Pathogens," PLoS ONE, 7(6):1-18.
Wen, A. et al. (Dec. 1, 2010) "The Role of the Transcription Factor CREB in Immune Function," J Immunol., 185(11):6413-6419.
Willuda, J. et al. (Jul. 1, 2019) "Abstract LB-075: Increased T cell-activation resulting from the combination of the anti-CEACAM6 function-blocking antibody BAY 1834942 with checkpoint inhibitors targeting either PD-1/PD-L1 or TIM-3," Cancer Res. 79(13, suppl.): 1-4.
Willuda, J. et al. (Jul. 2018) "Abstract 1771: BAY 1834942 is an immunotherapeutic antibody blocking the novel immune checkpoint regulator CEACAM6 (CD66c)," Cancer Res. 78(13, suppl. ):1-4.
Wittemer-Rump, S. et al. (2018). "Abstract 2791: Physiologically based pharmacokinetic modeling and simulations to estimate the efficacious dose of the CEACAM6 function-blocking antibodyBAY 1834942," Cancer Research, 78(13):1-6.
Witzens-Harig, M. et al. (2013). "Tumor cells in multiple myeloma patients inhibit myeloma-reactive T cells through carcinoembryonic antigen-related cell adhesion molecule-6," Blood, 121(22):4493-4503.
Wolchok, J. et al. (Jul. 11, 2013) "Safety and clinical activity of combined PD-1 (nivolumab) and CTLA-4 (ipilimumab) blockade in advanced melanoma patients," N Engl J Med., 369(2): 122-133.
Yang, L. et al. (2004). "Tumor-Host Immune Interactions and Dendritic Cell Dysfunction," Advances in Cancer Research, 13-27.
Office Action; China National Intellectual Property Administration; Chinese Application No. 201980078825.6; Dec. 28, 2023; 7 pages.
He, Y., et al., "TIM-3, a promising target for cancer immunotherapy", OncoTargets and Therapy, Oct. 2018, p. 7005-7009.
Du, W., et al., "TIM-3 as a Target for Cancer Immunotherapy and Mechanisms of Action", International Journal of Molecular Sciences, 2017, vol. 18, No. 3, p. 645.
Koyama, S., et al., "Adaptive resistance to therapeutic PD-1 blockade is associated with upregulation of alternative immune checkpoints", Nature Communications, 2016, vol. 7, No. 1, p. 10501.

* cited by examiner

SEQUENCE LISTING

<160> NUMBER OF SEQ ID NOS: 21

<210> SEQ ID NO 1
<211> LENGTH: 118
<212> TYPE: PRT
<213> ORGANISM: Artificial Sequence
<220> FEATURE:
<223> OTHER INFORMATION: Antibody sequence

<400> SEQUENCE: 1

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Ile Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115
```

<210> SEQ ID NO 2
<211> LENGTH: 7
<212> TYPE: PRT
<213> ORGANISM: Artificial Sequence
<220> FEATURE:
<223> OTHER INFORMATION: Antibody sequence

<400> SEQUENCE: 2

```
Thr Tyr Gly Ile Gly Val Gly
1               5
```

<210> SEQ ID NO 3
<211> LENGTH: 16
<212> TYPE: PRT
<213> ORGANISM: Artificial Sequence
<220> FEATURE:
<223> OTHER INFORMATION: Antibody sequence

<400> SEQUENCE: 3

```
His Ile Trp Trp Asn Asp Asn Lys Tyr Tyr Ser Thr Ser Leu Lys Thr
1               5                   10                  15
```

<210> SEQ ID NO 4
<211> LENGTH: 8
<212> TYPE: PRT
<213> ORGANISM: Artificial Sequence
<220> FEATURE:
<223> OTHER INFORMATION: Antibody sequence

<400> SEQUENCE: 4

```
Ile Ser Leu Pro Tyr Phe Asp Tyr
1               5
```

<210> SEQ ID NO 5
<211> LENGTH: 107
<212> TYPE: PRT

```
<213> ORGANISM: Artificial Sequence
<220> FEATURE:
<223> OTHER INFORMATION: Antibody sequence

<400> SEQUENCE: 5

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Antibody sequence

<400> SEQUENCE: 6

Lys Ala Ser Gln Asn Val Gly Thr Ala Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Antibody sequence

<400> SEQUENCE: 7

Ser Ala Ser Asn Arg Tyr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Antibody sequence

<400> SEQUENCE: 8

Gln Gln Tyr Ser Ser Tyr Pro Leu Thr
1               5

<210> SEQ ID NO 9
<211> LENGTH: 443
<212> TYPE: PRT
<213> ORGANISM: Artificial Sequence
<220> FEATURE:
<223> OTHER INFORMATION: Antibody sequence

<400> SEQUENCE: 9

Gln Val Thr Leu Arg Glu Ser Gly Pro Ala Leu Val Lys Pro Thr Gln
1               5                   10                  15
```

```
Thr Leu Thr Leu Thr Cys Thr Phe Ser Gly Phe Ser Leu Ser Thr Tyr
            20              25              30
Gly Ile Gly Val Gly Trp Ile Arg Gln Pro Pro Gly Lys Ala Leu Glu
        35              40              45
Trp Leu Ala His Ile Trp Trp Asn Asp Asn Lys Tyr Tyr Ser Thr Ser
    50              55              60
Leu Lys Thr Arg Leu Thr Ile Ser Lys Asp Thr Ser Lys Asn Gln Val
65              70              75              80
Val Leu Thr Met Thr Asn Met Asp Pro Val Thr Ala Thr Tyr Tyr
            85              90              95
Cys Ala Arg Ile Ser Leu Pro Tyr Phe Asp Tyr Trp Gly Gln Gly Thr
        100             105             110
Thr Leu Thr Val Ser Ser Ala Ser Thr Lys Gly Pro Ser Val Phe Pro
    115             120             125
Leu Ala Pro Cys Ser Arg Ser Thr Ser Glu Ser Thr Ala Ala Leu Gly
    130             135             140
Cys Leu Val Lys Asp Tyr Phe Pro Glu Pro Val Thr Val Ser Trp Asn
145             150             155             160
Ser Gly Ala Leu Thr Ser Gly Val His Thr Phe Pro Ala Val Leu Gln
            165             170             175
Ser Ser Gly Leu Tyr Ser Leu Ser Ser Val Val Thr Val Pro Ser Ser
            180             185             190
Asn Phe Gly Thr Gln Thr Tyr Thr Cys Asn Val Asp His Lys Pro Ser
            195             200             205
Asn Thr Lys Val Asp Lys Thr Val Glu Arg Lys Cys Cys Val Glu Cys
    210             215             220
Pro Pro Cys Pro Ala Pro Pro Val Ala Gly Pro Ser Val Phe Leu Phe
225             230             235             240
Pro Pro Lys Pro Lys Asp Thr Leu Met Ile Ser Arg Thr Pro Glu Val
            245             250             255
Thr Cys Val Val Val Asp Val Ser His Glu Asp Pro Glu Val Gln Phe
            260             265             270
Asn Trp Tyr Val Asp Gly Val Glu Val His Asn Ala Lys Thr Lys Pro
        275             280             285
Arg Glu Glu Gln Phe Asn Ser Thr Phe Arg Val Val Ser Val Leu Thr
    290             295             300
Val Val His Gln Asp Trp Leu Asn Gly Lys Glu Tyr Lys Cys Lys Val
305             310             315             320
Ser Asn Lys Gly Leu Pro Ala Pro Ile Glu Lys Thr Ile Ser Lys Thr
            325             330             335
Lys Gly Gln Pro Arg Glu Pro Gln Val Tyr Thr Leu Pro Pro Ser Arg
            340             345             350
Glu Glu Met Thr Lys Asn Gln Val Ser Leu Thr Cys Leu Val Lys Gly
            355             360             365
Phe Tyr Pro Ser Asp Ile Ala Val Glu Trp Glu Ser Asn Gly Gln Pro
    370             375             380
Glu Asn Asn Tyr Lys Thr Thr Pro Pro Met Leu Asp Ser Asp Gly Ser
385             390             395             400
Phe Phe Leu Tyr Ser Lys Leu Thr Val Asp Lys Ser Arg Trp Gln Gln
                405             410             415
Gly Asn Val Phe Ser Cys Ser Val Met His Glu Ala Leu His Asn His
            420             425             430
Tyr Thr Gln Lys Ser Leu Ser Leu Ser Pro Gly
```

```
                       435                 440

<210> SEQ ID NO 10
<211> LENGTH: 214
<212> TYPE: PRT
<213> ORGANISM: Artificial Sequence
<220> FEATURE:
<223> OTHER INFORMATION: Antibody sequence

<400> SEQUENCE: 10

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 113
<212> TYPE: PRT
<213> ORGANISM: Artificial Sequence
<220> FEATURE:
<223> OTHER INFORMATION: Antibody sequence

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ala Ser Gly Phe Thr Phe Ser Ser
            20                  25                  30

Tyr Asp Met Ser Trp Val Arg Gln Ala Pro Gly Lys Gly Leu Asp Trp
        35                  40                  45

Val Ser Thr Ile Ser Gly Gly Gly Thr Tyr Thr Tyr Tyr Gln Asp Ser
    50                  55                  60

Val Lys Gly Arg Phe Thr Ile Ser Arg Asp Asn Ser Lys Asn Thr Leu
65                  70                  75                  80
```

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser

<210> SEQ ID NO 12
<211> LENGTH: 5
<212> TYPE: PRT
<213> ORGANISM: Artificial Sequence
<220> FEATURE:
<223> OTHER INFORMATION: Antibody sequence

<400> SEQUENCE: 12

Ser Tyr Asp Met Ser
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody sequence

<400> SEQUENCE: 13

Thr Ile Ser Gly Gly Gly Thr Tyr Thr Tyr Tyr Gln Asp Ser Val Lys
1               5                   10                  15

Gly

<210> SEQ ID NO 14
<211> LENGTH: 3
<212> TYPE: PRT
<213> ORGANISM: Artificial Sequence
<220> FEATURE:
<223> OTHER INFORMATION: Antibody sequence

<400> SEQUENCE: 14

Met Asp Tyr
1

<210> SEQ ID NO 15
<211> LENGTH: 107
<212> TYPE: PRT
<213> ORGANISM: Artificial Sequence
<220> FEATURE:
<223> OTHER INFORMATION: Antibody sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser His Ser Ala Pro Leu
                85                  90                  95

Thr Phe Gly Gly Gly Thr Lys Val Glu Ile Lys
            100                 105

<210> SEQ ID NO 16
<211> LENGTH: 11
<212> TYPE: PRT
<213> ORGANISM: Artificial Sequence
<220> FEATURE:
<223> OTHER INFORMATION: Antibody sequence

<400> SEQUENCE: 16

Arg Ala Ser Gln Ser Ile Arg Arg Tyr Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Antibody sequence

<400> SEQUENCE: 17

Gly Ala Ser Thr Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Antibody sequence

<400> SEQUENCE: 18

Gln Gln Ser His Ser Ala Pro Leu Thr
1               5

<210> SEQ ID NO 19
<211> LENGTH: 440
<212> TYPE: PRT
<213> ORGANISM: Artificial Sequence
<220> FEATURE:
<223> OTHER INFORMATION: Antibody sequence

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ala Ser Gly Phe Thr Phe Ser Ser
            20                  25                  30

Tyr Asp Met Ser Trp Val Arg Gln Ala Pro Gly Lys Gly Leu Asp Trp
        35                  40                  45

Val Ser Thr Ile Ser Gly Gly Gly Thr Tyr Tyr Tyr Gln Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 20
<211> LENGTH: 214
<212> TYPE: PRT
<213> ORGANISM: Artificial Sequence
<220> FEATURE:
<223> OTHER INFORMATION: Antibody sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
            35                  40                  45

Tyr Gly Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

```
Glu Asp Phe Ala Val Tyr Tyr Cys Gln Gln Ser His Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gly Ile Leu Gly Phe Val Phe Thr Leu
1               5
```

PHARMACEUTICAL COMBINATION OF ANTI CEACAM6 AND TIM3 ANTIBODIES

CROSS REFERENCE TO RELATED APPLICATIONS

This application is a national stage application under 35 U.S.C. § 371 of International Application No. PCT/EP2019/084849, filed internationally on Dec. 12, 2019, which claims the benefit of European Application No. 18214059.0, filed Dec. 19, 2018.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052049500SEQLIST.TXT, date recorded: Jun. 3, 2021, size: 18,713 bytes).

The present invention relates to combinations of at least two components, component A and component B, component A being anti-CEACAM6 antibody TPP-3310 and component B being an anti-TIM-3 antibody, preferentially cobolimab, MBG-453, BMS-986258, Sym-023, LY-3321367 or INCAGN-2390.

Another aspect of the present invention relates to the use of such combinations as described herein for the preparation of a medicament for the treatment or prophylaxis of cancer.

Yet another aspect of the present invention relates to methods of treatment or prophylaxis of a cancer in a subject, comprising administering to said subject a therapeutically effective amount of a combination as described herein.

Further, the present invention relates to a kit comprising a combination of:
- a components A, being anti-CEACAM6 antibody TPP-3310;
- a component B, being preferentially cobolimab, MBG-453, BMS-986258, Sym-023, LY-3321367 or INCAGN-2390, and optionally
- one or more pharmaceutical agents C;

in which optionally either or both of said components A and B are in the form of a pharmaceutical formulation which is ready for use to be administered simultaneously, concurrently, separately or sequentially.

Component A and B preferably are administered by the intravenous route.

In some embodiments the cancer is lung cancer, in particular non-small cell lung cancer (NSCLC), pancreatic cancer, gastric cancer, colorectal cancer, head and neck cancer, bladder cancer, bile duct cancer, breast cancer, cervical cancer, esophageal cancer.

BACKGROUND TO THE INVENTION

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

T-cell responses against tumor-associated antigens have been described in many tumors and often cause an accumulation of tumor specific memory T cells in lymphoid organs or in the blood. However, the capacity of T cells to react against autologous tumor cells is generally low. Many tumors have the capacity to block effector functions of T cells which contributes to the limited activity of tumor immunotherapy. T-cell unresponsiveness against tumor cells has been demonstrated for a broad variety of cancers.

The immune system depends on multiple checkpoints or "immunological brakes" to avoid over-activation of the immune system on healthy cells. Tumor cells often take advantage of these checkpoints to escape detection by the immune system. CTLA-4 and PD-1 are checkpoints that have been studied as targets for cancer therapy.

Checkpoint proteins regulate T-cell activation or function. Numerous checkpoint proteins are known, such as CTLA-4 and its ligands CD80 and CD86; and PD-1 with its ligands PD-L1 and PD-L2. Novel checkpoint proteins described are TIM-3, LAG-3 and others. These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. Currently, different immunotherapeutic approaches are standing their ground as powerful treatment strategies for a wide range of malignant diseases.

A very prominent and recent example of an outstanding cancer immunotherapy success involves immune checkpoint blockade therapy by monoclonal antibodies (mAb) targeting inhibitory molecules on either immune effector T-cells or antigen presenting cells including tumor cells. Interfering with co-inhibitors has been shown to unleash a powerful antitumor T-cell response (Pardoll: The blockade of immune checkpoints in cancer immunotherapy. Nat Rev Cancer 12: (2012) 252-264).

CTLA-4 has been shown to be aberrantly upregulated and present on the surface of T cells in certain cancers, dampening T-cell activation in response to tumor cells. PD-1 is another immunologic checkpoint that has been found to be upregulated in certain tumors; it inhibits T-cell function contributing to the tumor's ability to evade the immune system.

Antibody blockade of immune checkpoint molecules for immune cell activation is a clinically validated approach. In 2011 the CTLA-4 blocking antibody Ipilimumab has been approved by the FDA for the 2nd line therapy of metastatic melanoma (Yervoy). Another example is the blockade of the PD-1/PD-L1 axis for which several drugs are either approved or currently under clinical development and for which impressive clinical responses have been reported in melanoma, lung cancer, RCC, bladder cancer and others (Shen and Zhao: Efficacy of PD-1 and PD-L1 inhibitors and PD-L1 expression status in cancer: meta-analysis. BMJ 2018; 362: k3529).

In 2013, a combination of anti-CTLA4 and anti-PD1 mAb treatment was reported to act synergistically in increasing survival and tumor regression in advanced melanoma patients (Wolchok et al.: Nivolumab plus ipilimumab in advanced melanoma. N Engl J Med 369: (2013) 122-133).

Anti-TIM-3 monoclonal antibodies are in phase II and in phase I clinical development (clinicaltrials.gov). Their clinical relevance and potential is described e.g. in Marin- Acevedo et al. "Next generation of immune checkpoint therapy in cancer: new developments and challenges", 2018 Journal of Hematology & Oncology 11:39 and Buruguru et al., "Emerging targets in cancer immunotherapy", Seminars in Cancer Biology 52 (2018): 39-52.

CEACAM6 contributes to the regulation of CD8+ T cell response as well. In multiple myeloma expressing several CEACAM family members treatment with anti-CEACAM6 mAbs or siRNA silencing CEACAM6 reinstated T cell reactivity against malignant plasma cells indicating a role for CEACAM6 in CD8+ T cell response regulation (Witzens-Harig et al., Blood 2013 May 30; 121(22):4493-503). Very potent anti-CECAM6 antibodies for cancer immunotherapy including TPP-3310 were disclosed in WO 2016/150899 A2.

DEFINITIONS

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent with the meaning commonly understood in the art. Such references include, but are not limited to, Singleton et al., Dictionary of Microbiology and Molecular Biology (2nd ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2nd Edition, W.B. Saunders Company. Any additional technical resource available to the person of ordinary skill in the art providing definitions of terms used herein having the meaning commonly understood in the art can be consulted. For the purposes of the present invention, the following terms are further defined. Additional terms are defined elsewhere in the description. As used herein and in the appended claims, the singular forms "a," and "the" include plural reference unless the context clearly dictates otherwise. Thus, for example, reference to "a gene" is a reference to one or more genes and includes equivalents thereof known to those skilled in the art, and so forth.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprised of four polypeptide chains, two heavy (H) chains and two light (L) chains which are typically inter-connected by disulfide bonds. Each heavy chain is comprised of a heavy chain variable region (abbreviated herein as VH) and a heavy chain constant region. The heavy chain constant region can comprise e.g. three domains CH1, CH2 and CH3. Each light chain is comprised of a light chain variable region (abbreviated herein as VL) and a light chain constant region. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs arranged from amino-terminus to carboxy-terminus e.g. in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (e.g. about residues 24-34 (L-CDR1), 50-56 (L-CDR2) and 89-97 (L-CDR3) in the light chain variable domain and 31-35 (H-CDR1), 50-65 (H-CDR2) and 95-102 (H-CDR3) in the heavy chain variable domain; (Kabat et al., Sequences of Proteins of Immulological Interest, 5th Ed. Public Health Service, National Institutes of Health, Bethesda, MD. (1991)) and/or those residues from a "hypervariable loop" (e.g. about residues 26-32 (L-CDR1), 50-52 (L-CDR2) and 91-96 (L-CDR3) in the light chain variable domain and 26-32 (H-CDR1), 53-55 (H-CDR2) and 96-101 (H-CDR3) in the heavy chain variable domain (Chothia and Lesk; J Mol Biol 196: 901-917 (1987)). In some instances, a complementarity determining region can include amino acids from both a CDR region defined according to Kabat and a hypervariable loop.

Depending on the amino acid sequence of the constant domain of their heavy chains, intact antibodies can be assigned to different "classes". There are five major classes of intact antibodies: IgA, IgD, IgE, IgG, and IgM, and several of these maybe further divided into "subclasses" (isotypes), e.g., IgG1, IgG2, IgG3, IgG4, IgA1, and IgA2. A preferred class of immunoglobulins for use in the present invention is IgG.

The heavy-chain constant domains that correspond to the different classes of antibodies are called [alpha], [delta], [epsilon], [gamma], and [mu], respectively. The subunit structures and three-dimensional configurations of different classes of immunoglobulins are well known. As used herein antibodies are conventionally known antibodies and functional fragments thereof.

An "anti-antigen" antibody refers to an antibody that binds specifically to the antigen. For example, an anti-PD-1 antibody binds specifically to PD-1, an anti-CECAM6 antibody binds specifically to CECAM6, and an anti-TIM-3 antibody binds specifically to TIM-3.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. Specific binding of an antibody or binder does not exclude the antibody or binder binding to a plurality of antigens/target molecules (e.g. orthologs of different species). The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

"Functional fragments", "antigen-binding antibody fragments", or "antibody fragments" refer to one or more fragments of an antibody that retain the ability to bind specifically to the antigen bound by the whole antibody. "Functional fragments", "antigen-binding antibody fragments", or "antibody fragments" of the invention include but are not limited to Fab, Fab', Fab'-SH, F(ab')2, and Fv fragments; diabodies; single domain antibodies (DAbs); linear antibodies; single-chain antibody molecules (scFv); and multispecific, such as bi- and tri-specific, antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag).

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

As used herein "CEACAM6" designates the "carcinoembryonic antigen-related cell adhesion molecule 6", also known as "CD66c" (Cluster of Differentiation 66c), or Non-specific crossreacting antigen, or NCA, or NCA-50/90. CEACAM6 is a glycosylphosphatidylinositol (GPI)-linked cell surface protein involved in cell-cell adhesion. The term "CEACAM6" as used herein includes human CEACAM6 (hCEACAM6), variants, isoforms, and species homologs of hCEACAM6, and analogs having at least one common epitope with hCEACAM6. A reference sequence for human CEACAM6 is available from UniProtKB/Swiss-Prot data base under accession number P40199.3

"Programmed Death-1 (PD-1)" refers to an immunoinhibitory receptor belonging to the CD28 family. PD-1 is expressed predominantly on previously activated T cells in vivo and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that down regulate T cell activation and cytokine secretion upon binding to PD-1. The term "PD-L1" as used herein includes human PD-L1 (hPDL1), variants, isoforms, and species homologs of hPD-L1, and analogs having at least one common epitope with hPD-L1. The complete hPD-L1 sequence can be found under GenBank Accession No. Q9NZQ7.

As used herein "TIM-3" designates the "T cell immunoglobulin domain and mucin domain 3" (also known as HAVCAR2) a member of the TIM-family. TIM-3 is a transmembrane protein on the cell surface. It has been described as an activation-induced inhibitory molecule involved in tolerance and shown to induce T cell exhaustion. The term "TIM-3" as used herein includes human TIM-3 (hTIM-3), variants, isoforms, and species homologs of hTIM-3, and analogs having at least one common epitope with hTIM-3. A reference sequence for human TIM-3 is available from UniProtKB/Swiss-Prot data base under accession number UniProtKB Q8TDQ0 (HAVR2_HUMAN) and NCBI database, NCBI Reference Sequence: NP_116171.3.

As used herein, the terms "patient" or "subject" are used interchangeably and mean a mammal, including, but not limited to, a human or non-human mammal, such as a bovine, equine, canine, ovine, or feline. Preferably, the patient is a human.

DESCRIPTION OF THE INVENTION

Surprisingly it was observed that a combination of a TIM-3 immune checkpoint inhibitor and anti-CECAM6 antibody TPP-3310 acts much more than additive in an in vitro assay performed to evaluate the therapeutic potential of drug combinations for tumor regression. This effect was surprisingly even stronger than the combination of a PD-1 or a PD-L1 immune checkpoint inhibitor with the anti-CEACAM6 antibody TPP-3310.

Therefore the present invention provides combinations of at least two components, component A and component B, component A being anti-CEACAM6 antibody TPP-3310 and component B being an anti-TIM-3 antibody, preferentially cobolimab, MBG-453, BMS-986258, Sym-023, LY-3321367 or INCAGN-2390.

The combinations comprising at least two components A and B, as described and defined herein are also referred to as "combinations of the present invention".

Further, the present invention relates to a kit comprising: a combination of:
  a component A, being anti-CEACAM6 antibody TPP-3310;
  a component B, being an anti-TIM-3 antibody, preferentially cobolimab, MBG-453, BMS-986258, Sym-023, LY-3321367 or INCAGN-2390, and optionally
  one or more pharmaceutical agents C;
in which optionally either or both of said components A and B are in the form of a pharmaceutical formulation which is ready for use to be administered simultaneously, concurrently, separately or sequentially.

The invention further provides an anti-CEACAM6 antibody (component A) for use in simultaneous, separate, or sequential combination with an anti-TIM-3 antibody (component B) in the treatment of cancer, wherein the anti-CEACAM6 antibody comprises the H-CDR1, H-CDR2, H-CDR3, L-CDR1, L-CDR2, and L-CDR3 of antibody TPP-3310.

The invention further provides an anti-CEACAM6 antibody (component A) for use in simultaneous, separate, or sequential combination with an anti-TIM-3 antibody (component B) in the treatment of cancer, wherein the anti- CEACAM6 antibody comprises the variable heavy chain sequence and a variable light chain sequences of antibody TPP-3310.

The invention further provides an anti-CEACAM6 antibody (component A) for use in simultaneous, separate, or sequential combination with an anti-TIM-3 antibody (component B) in the treatment of cancer, wherein the anti-CEACAM6 antibody comprises the heavy chain region and light chain region of antibody TPP-3310.

The invention further provides the anti-CEACAM6 antibody TPP-3310 (component A) for use in simultaneous, separate, or sequential combination with an anti-TIM-3 antibody (component B) in the treatment of cancer, wherein the anti-TIM-3 antibody is cobolimab, MBG-453, BMS-986258, Sym-023, LY-3321367 or INCAGN-2390.

The invention further provides the anti-CEACAM6 antibody TPP-3310 (component A) for use in simultaneous, separate, or sequential combination with an anti-TIM-3 antibody (component B) in the treatment of cancer, wherein the cancer is lung cancer, in particular non-small cell lung cancer, ovarian cancer, mesothelioma, pancreatic cancer, gastric cancer, colorectal cancer, head and neck cancer, bladder cancer, bile duct cancer, breast cancer, cervical cancer, or esophageal cancer.

The invention further provides the anti-CEACAM6 antibody TPP-3310 (component A) for use in simultaneous, separate, or sequential combination with an anti-TIM-3 antibody (component B) in the treatment of cancer, wherein at least one of the anti-CEACAM6 antibody or the anti-TIM-3 antibody is administered in simultaneous, separate, or sequential combination with one or more pharmaceutical agents (agents C).

The invention further provides a method of treating cancer comprising administering to a patient in need, thereof an effective amount of anti-CEACAM6 antibody TPP-3310 (component A) in simultaneous, separate, or sequential combination with an anti-TIM-3 antibody (component B).

The invention further provides a method of treating cancer comprising administering to a patient in need, thereof an effective amount of anti-CEACAM6 antibody TPP-3310 (component A) in simultaneous, separate, or sequential combination with an anti-TIM-3 antibody (component B), wherein the anti-TIM-3 antibody is cobolimab, MBG-453, BMS-986258, Sym-023, LY-3321367 or INCAGN-2390.

The invention further provides the use of anti-CEACAM6 antibody TPP-3310 (component A) for the manufacture of a medicament for the treatment of cancer in simultaneous, separate, or sequential combination with an anti-TIM-3 antibody (component B).

The invention further provides the use of anti-CEACAM6 antibody TPP-3310 (component A) for the manufacture of a medicament for the treatment of cancer in simultaneous, separate, or sequential combination with an anti-TIM-3 antibody (component B), wherein the anti-TIM-3 antibody is cobolimab, MBG-453, BMS-986258, Sym-023, LY-3321367 or INCAGN-2390.

The components may be administered independently of one another by the oral, intravenous, topical, local installations, intraperitoneal or nasal route.

In accordance with another aspect, the present invention covers the combinations as described supra for the treatment or prophylaxis of cancer.

In accordance with another aspect, the present invention covers the use of such combinations as described supra for the preparation of a medicament for the treatment or prophylaxis of cancer.

Component A of the Combination

Component A is anti-CEACAM6 antibody TPP-3310 which was disclosed in WO 2016/150899 A2. Further anti-CECAM6 antibodies disclosed in WO 2016150899 A2 are for example TPP-3714, TPP-3820, TPP-3821, TPP-3707, and TPP-3705. These antibodies are human or humanized antibodies binding human CEACAM6 with high affinity, are cross-reactive to monkey CEACAM6, do not bind to any paralogs, especially CEACAM1, CEACAM3, and CEACAM5, and are able to relieve CEACAM6-mediated immunosuppression.

The term "anti-CEACAM6 antibody" relates to an antibody which specifically binds the cancer target molecule CEACAM6, preferentially with an affinity which is sufficient for a diagnostic and/or therapeutic application. In certain embodiments, the anti-CEACAM6 antibody binds to an epitope which is conserved between different species.

TPP-3310 is an antibody which comprises H-CDR1 comprising the amino acid sequence of SEQ ID NO: 2, H-CDR2 comprising the amino acid sequence of SEQ ID NO: 3, H-CDR3 comprising the amino acid sequence of SEQ ID NO: 4, L-CDR1 comprising the amino acid sequence of SEQ ID NO: 6, L-CDR2 comprising the amino acid sequence of SEQ ID NO: 7, and L-CDR3 comprising the amino acid sequence of SEQ ID NO: 8.

Preferably TPP-3310 is an antibody which comprises a variable heavy chain sequence (VH) of SEQ ID NO:1 and a variable light chain sequences (VL) of SEQ ID NO:5.

Highly preferred, TPP-3310 is an antibody which comprises a heavy chain region (HC) of SEQ ID NO: 9 and a light chain region (LC) of SEQ ID NO: 10.

Component B of the Combination

Component B is an antibody or an antigen-binding portion thereof that binds specifically to a TIM-3 receptor and inhibits TIM-3 activity ("anti-TIM-3 antibody").

Anti-TIM-3 Antibody

In certain embodiments the anti-TIM-3 antibody or an antigen-binding portion thereof is cobolimab (TSR-022, Tesaro), or has the same CDR regions as cobolimab. Cobolimab is a TIM-3 immune checkpoint inhibitor antibody that selectively prevents interaction with some of the known TIM-3 ligands (HMGB1, Galectin-9, Phosphatidylserine (PS), thereby blocking the down-regulation of antitumor T-cell functions. Cobolimab is described, for example, in WO2016161270 A1 and WO 2018129553 A1. Cobolimab is currently in clinical trials; ClinicalTrials.gov Identifier: NCT02817633 and NCT03680508.

In other embodiments the anti-TIM-3 antibody or an antigen-binding portion thereof is MBG-453 (Novartis) or has the same CDR regions as MBG-453. MBG-453 is a TIM-3 immune checkpoint inhibitor antibody that selectively prevents interaction with some of the known TIM-3 ligands (HMGB1, Galectin-9, Phosphatidylserine (PS), thereby blocking the down-regulation of antitumor T-cell functions. MBG-453 is described, for example, in WO 2015117002 A1. MBG-453 is registered under CAS No: 2128742-61-8. MBG-453 is currently in clinical trials; ClinicalTrials.gov Identifier: NCT02608268 and NCT03066648.

In other embodiments the anti-TIM-3 antibody or an antigen-binding portion thereof is BMS-986258 (Bristol-Myers Squibb, Five Prime), or has the same CDR regions as BMS-986258. BMS-986258 is a TIM-3 immune checkpoint inhibitor antibody that selectively prevents interaction with some of the known TIM-3 ligands (HMGB1, Galectin-9, Phosphatidylserine (PS), thereby blocking the down-regulation of antitumor T-cell functions. BMS-986258 is currently in clinical trials; ClinicalTrials.gov Identifier: NCT03446040. BMS-986258 is described, for example, in WO 2018013818 A2.

In other embodiments the anti-TIM-3 antibody or an antigen-binding portion thereof is Sym-023 (Symphogen), or has the same CDR regions as Sym-023. Sym-023, is a TIM-3 immune checkpoint inhibitor antibody that selectively prevents interaction with some of the known TIM-3 ligands (HMGB1, Galectin-9, Phosphatidylserine (PS), thereby blocking the down-regulation of antitumor T-cell functions. Sym-023 is currently in clinical trials; ClinicalTrials.gov Identifier: NCT03489343. Sym-023 is described, for example, in WO 2017178493 A1.

In other embodiments the anti-TIM-3 antibody or an antigen-binding portion thereof is LY-3321367 (Eli Lilly), or has the same CDR regions as LY-3321367. LY-3321367 is a TIM-3 immune checkpoint inhibitor antibody that selectively prevents interaction with some of the known TIM-3 ligands (HMGB1, Galectin-9, Phosphatidylserine (PS), thereby blocking the down-regulation of antitumor T-cell functions. LY-3321367 is currently in clinical trials; ClinicalTrials.gov Identifier: NCT03099109. LY-3321367 is described, for example, in WO 2018039020 A1.

In other embodiments the anti-TIM-3 antibody or an antigen-binding portion thereof is INCAGN-2390 (Agenus), or has the same CDR regions as INCAGN-2390. INCAGN-2390 is a TIM-3 immune checkpoint inhibitor antibody that selectively prevents interaction with some of the known TIM-3 ligands (HMGB1, Galectin-9, Phosphatidylserine (PS), thereby blocking the down-regulation of antitumor T-cell functions. INCAGN-2390 is currently in clinical trials; ClinicalTrials.gov Identifier: NCT03652077. INCAGN-2390 is described, for example, in WO 2017205721 A1.

In other embodiments the anti-TIM-3 antibody or an antigen-binding portion thereof is MAB2365 from R&D Jackson Immunoresearch, or has the same CDR regions as MAB2365. MAB2365 is an rIgG2 antibody.

In certain embodiments, the anti-TIM-3 antibody comprises:
  (i) H-CDR1 comprising the amino acid sequence of SEQ ID NO: 12, H-CDR2 comprising the amino acid sequence of SEQ ID NO: 13, H-CDR3 comprising the amino acid sequence of SEQ ID NO: 14, L-CDR1 comprising the amino acid sequence of SEQ ID NO: 16, L-CDR2 comprising the amino acid sequence of SEQ ID NO: 17, and L-CDR3 comprising the amino acid sequence of SEQ ID NO: 18.

In certain embodiments, the anti-TIM-3 antibody comprises:
  (i) a variable heavy chain sequence (VH) of SEQ ID NO:11 and a variable light chain sequences (VL) of SEQ ID NO:15.

In certain embodiments, the anti-TIM-3 antibody comprises:
  (i) a heavy chain region (HC) of SEQ ID NO: 19 and a light chain region (LC) of SEQ ID NO: 20.

Production of Antibodies

Antibodies or antigen-binding antibody fragments which bind target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 8610029-10033, 1989 or in WO 90/0786. Furthermore, processes for recombinant expression of proteins in general and of antibodies in particular are known to the person skilled in the art (see, for example, in Berger and Kimmel (Guide to Molecular Cloning Techniques, Methods in Enzymology, Vol. 152, Academic Press, Inc.); Sambrook, et al., (Molecular Cloning A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies A Laboratory Manual, Cold Spring Harbor Laboratory Press (19881, Paul [Ed.]); Fundamental Immunology, (Lippincott Williams & Wilkins (1998)); and Harlow, et al., (Using Antibodies A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Bacterial Expression

The person skilled in the art is aware of the way in which antibodies, antigen-binding fragments thereof or variants thereof can be produced with the aid of bacterial expression.

Suitable expression vectors for bacterial expression of desired proteins are constructed by insertion of a DNA sequence which encodes the desired protein within the functional reading frame together with suitable translation initiation and translation termination signals and with a functional promoter. The vector comprises one or more phenotypically selectable markers and a replication origin in order to enable the retention of the vector and, if desired, the amplification thereof within the host. Suitable prokaryotic hosts for transformation include but are not limited to *E. coli, Bacillus subtilis, Salmonella typhimurium* and various species from the genus *Pseudomonas, Streptomyces*, and *Staphylococcus*. Bacterial vectors may be based, for example, on bacteriophages, plasmids, or phagemids. These vectors may contain selectable markers and a bacterial replication origin, which are derived from commercially available plasmids. Many commercially available plasmids typically contain elements of the well-known cloning vector pBR322 (ATCC 37017). In bacterial systems, a number of advantageous expression vectors can be selected on the basis of the intended use of the protein to be expressed.

After transformation of a suitable host strain and growth of the host strain to an appropriate cell density, the selected promoter is de-repressed/induced by suitable means (for example a change in temperature or chemical induction), and the cells are cultivated for an additional period. The cells are typically harvested by centrifugation and if necessary digested in a physical manner or by chemical means, and the resulting raw extract is retained for further purification.

Mammalian Cell Expression

The person skilled in the art is aware of the way in which antibodies, antigen-binding fragments thereof or variants thereof can be produced with the aid of mammalian cell expression.

Preferred regulatory sequences for expression in mammalian cell hosts include viral elements which lead to high expression in mammalian cells, such as promoters and/or expression amplifiers derived from cytomegalovirus (CMV) (such as the CMV promoter/enhancer), simian virus 40 (SV40) (such as the SV40 promoter/enhancer), from adenovirus, (for example the adenovirus major late promoter (AdMLP)) and from polyoma. The expression of the antibodies may be constitutive or regulated (for example induced by addition or removal of small molecule inductors such as tetracycline in combination with the Tet system).

For further description of viral regulatory elements and sequences thereof, reference is made, for example, to U.S. Pat. No. 5,168,062 by Stinski, U.S. Pat. No. 4,510,245 by Bell et al. and U.S. Pat. No. 4,968,615 by Schaffner et al. The recombinant expression vectors may likewise include a replication origin and selectable markers (see, for example, U.S. Pat. Nos. 4,399,216, 4,634,665 and 5,179,017). Suitable selectable markers include genes which impart resistance to substances such as G418, puromycin, hygromycin, blasticidin, zeocin/bleomycin, or methotrexate, or selectable markers which lead to auxotrophy of a host cell, such as glutamine synthetase (Bebbington et al., Biotechnology (N Y). 1992 February; 10(2):169-75), when the vector has been introduced into the cell.

For example, the dihydrofolate reductase (DHFR) gene imparts resistance to methotrexate, the neo gene imparts resistance to G418, the bsd gene from *Aspergillus terreus* imparts resistance to blasticidin, puromycin N-acetyltransferase imparts resistance to puromycin, the Sh ble gene product imparts resistance to zeocin, and resistance to hygromycin is imparted by the *E. coli* hygromycin resistance gene (hyg or hph). Selectable markers such as DHFR or glutamine synthetase are also helpful for amplification techniques in conjunction with MTX and MSX.

The transfection of an expression vector into a host cell can be executed with the aid of standard techniques, including by electroporation, nucleofection, calcium phosphate precipitation, lipofection, polycation-based transfection such as polyethyleneimine (PEI)-based transfection and DEAE-dextran transfection.

Suitable mammalian host cells for the expression of antibodies, antigen-binding fragments thereof, or variants thereof include Chinese hamster ovary (CHO) cells such as CHO-K1, CHO-S, CHO-K1SV [including DHFR-CHO cells, described in Urlaub and Chasin, (1980) Proc. Natl. Acad. Sci. USA 77:4216-4220 and Urlaub et al., Cell. 1983 June; 33(2):405-12, used with a DHFR-selectable marker, as described in R. J. Kaufman and P. A. Sharp (1982) Mol. Biol. 159:601-621, and other knockout cells, as detailed in Fan et al., Biotechnol Bioeng. 2012 April; 109(4):1007-15), NS0 myeloma cells, COS cells, HEK293 cells, HKB11 cells, BHK21 cells, CAP cells, EB66 cells, and SP2 cells.

The expression of antibodies, antigen-binding fragments thereof, or variants thereof can also be effected in a transient or semi-stable manner in expression systems such as HEK293, HEK293T, HEK293-EBNA, HEK293E, HEK293-6E, HEK293 Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for example like Durocher et al., Nucleic Acids Res. 2002 Jan. 15; 30(2): E9).

In some embodiments, the expression vector is constructed in such a way that the protein to be expressed is secreted into the cell culture medium in which the host cells are growing. The antibodies, the antigen-binding fragments thereof, or the variants thereof can be obtained from the cell culture medium with the aid of protein purification methods known to those skilled in the art.

Purification

The antibodies, the antigen-binding fragments thereof, or the variants thereof can be obtained and purified from recombinant cell cultures with the aid of well-known methods, examples of which include ammonium sulfate or ethanol precipitation, acid extraction, protein A chromatography, protein G chromatography, anion or cation exchange chromatography, phosphocellulose chromatography, hydrophobic interaction chromatography (HIC), affinity chromatography, hydroxyapatite chromatography and lectin chromatography. High-performance liquid chromatography ("HPLC") can likewise be employed for purification. See, for example, Colligan, Current Protocols in Immunology, or Current Protocols in Protein Science, John Wiley & Sons, NY, N.Y., (1997-2001), e.g., Chapters 1, 4, 6, 8, 9, 10.

Antibodies of the present invention or antigen-binding fragments thereof, or variants thereof include naturally purified products, products from chemical synthesis methods and products which are produced with the aid of recombinant techniques in prokaryotic or eukaryotic host cells. Eukaryotic hosts include, for example, yeast cells, higher plant cells, insect cells and mammalian cells. Depending on the host cell chosen for the recombinant expression, the protein expressed may be in glycosylated or non-glycosylated form.

In a preferred embodiment, the antibody is purified (1) to an extent of more than 95% by weight, measured, for example, by the Lowry method, by UV-vis spectroscopy or by SDS capillary gel electrophoresis (for example with a Caliper LabChip GXII, GX 90 or Biorad Bioanalyzer instrument), and in more preferred embodiments more than 99% by weight, (2) to a degree suitable for determination of at least 15 residues of the N-terminal or internal amino acid sequence, or (3) to homogeneity determined by SDS-PAGE under reducing or non-reducing conditions with the aid of Coomassie blue or preferably silver staining.

Usually, an isolated antibody is obtained with the aid of at least one protein purification step.

TABLE 1

Protein sequences of preferred antibodies

| TPP-ID | Antibody [Name] | SEQ ID NO: VH Protein | SEQ ID NO: H-CDR1 | SEQ ID NO: H-CDR2 | SEQ ID NO: H-CDR3 | SEQ ID NO: VL Protein | SEQ ID NO: L-CDR1 | SEQ ID NO: L-CDR2 | SEQ ID NO: L-CDR3 | SEQ ID NO: IgG Heavy Chain | SEQ ID NO: IgG Light Chain |
|---|---|---|---|---|---|---|---|---|---|---|---|
| TPP-3310 | aCECAM6 | 1 | 2 | 3 | 4 | 5 | 6 | 7 | 8 | 9 | 10 |
| TPP-18285 | Cobolimab (TSR-022) | 11 | 12 | 13 | 14 | 15 | 16 | 17 | 18 | 19 | 20 |

TABLE 2

Sequences of preferred antibodies

| "TPP-ID" | Antibody [Name] | Region | SEQ ID | Sequence |
|---|---|---|---|---|
| TPP-3310 | aCECAM6 | VH | SEQ ID NO:1 | QVTLRESGPALVKPTQTLTLTCTFSGFSLSTYGIGVGWIRQPPGKALEWLAHIWWNDNKYYSTSLKTRLTISKDTSKNQVVLTMTNMDPVDTATYYCARISLPYFDYWGQGTTLTVSS |
| TPP-3310 | aCECAM6 | HCDR1 | SEQ ID NO: 2 | TYGIGVG |
| TPP-3310 | aCECAM6 | HCDR2 | SEQ ID NO: 3 | HIWWNDNKYYSTSLKT |
| TPP-3310 | aCECAM6 | HCDR3 | SEQ ID NO: 4 | ISLPYFDY |
| TPP-3310 | aCECAM6 | VL | SEQ ID NO: 5 | DIQLTQSPSFLSASVGDRVTITCKASQNVGTAVAWYQQKPGKAPKLLIYSASNRYTGVPSRFSGSGSGTEFTLTISSLQPEDFATYYCQQYSSYPLTFGGGTKVEIK |
| TPP-3310 | aCECAM6 | LCDR1 | SEQ ID NO: 6 | KASQNVGTAVA |
| TPP-3310 | aCECAM6 | LCDR2 | SEQ ID NO: 7 | SASNRYT |
| TPP-3310 | aCECAM6 | LCDR3 | SEQ ID NO: 8 | QQYSSYPLT |
| TPP-3310 | aCECAM6 | Heavy Chain | SEQ ID NO: 9 | QVTLRESGPALVKPTQTLTLTCTFSGFSLSTYGIGVGWIRQPPGKALEWLAHIWWNDNKYYSTSLKTRLTISKDTSKNQVVLTMTNMDPVDTATYYCARISLPYFDYWGQGTTLTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| TPP-3310 | aCECAM6 | Light Chain | SEQ ID NO: 10 | DIQLTQSPSFLSASVGDRVTITCKASQNVGTAVAWYQQKPGKAPKLLIYSASNRYTGVPSRFSGSGSGTEFTLTISSLQPEDFATYYCQQYSSYPLTFGGGTKVEIKRTVAAPSVFIFPPSDEQLK |

TABLE 2-continued

Sequences of preferred antibodies

| "TPP-ID" | Antibody [Name] | Region | SEQ ID | Sequence |
|---|---|---|---|---|
| | | | | SGTASVVCLLNNFYPREAKVQWKV DNALQSGNSQESVTEQDSKDSTYS LSSTLTLSKADYEKHKVYACEVTHQ GLSSPVTKSFNRGEC |
| TPP-18285 | Cobolimab (TSR-022) | VH | SEQ ID NO: 11 | EVQLLESGGGLVQPGGSLRLSCAA ASGFTFSSYDMSWVRQAPGKGLD WVSTISGGGTYTYYQDSVKGRFTIS RDNSKNTLYLQMNSLRAEDTAVYY CASMDYWGQGTTVTVSS |
| TPP-18285 | Cobolimab (TSR-022) | HCDR1 | SEQ ID NO: 12 | SYDMS |
| TPP-18285 | Cobolimab (TSR-022) | HCDR2 | SEQ ID NO: 13 | TISGGGTYTYYQDSVKG |
| TPP-18285 | Cobolimab (TSR-022) | HCDR3 | SEQ ID NO: 14 | MDY |
| TPP-18285 | Cobolimab (TSR-022) | VL | SEQ ID NO: 15 | DIQMTQSPSSLSASVGDRVTITCRA SQSIRRYLNWYHQKPGKAPKLLIYG ASTLQSGVPSRFSGSGSGTDFTLTI SSLQPEDFAVYYCQQSHSAPLTFG GGTKVEIK |
| TPP-18285 | Cobolimab (TSR-022) | LCDR1 | SEQ ID NO: 16 | RASQSIRRYLN |
| TPP-18285 | Cobolimab (TSR-022) | LCDR2 | SEQ ID NO: 17 | GASTLQS |
| TPP-18285 | Cobolimab (TSR-022) | LCDR3 | SEQ ID NO: 18 | QQSHSAPLT |
| TPP-18285 | Cobolimab (TSR-022) | Heavy Chain | SEQ ID NO: 19 | EVQLLESGGGLVQPGGSLRLSCAA ASGFTFSSYDMSWVRQAPGKGLD WVSTISGGGTYTYYQDSVKGRFTIS RDNSKNTLYLQMNSLRAEDTAVYY CASMDYWGQGTTVTVSSASTKGPS VFPLAPCSRSTSESTAALGCLVKDY FPEPVTVSWNSGALTSGVHTFPAVL QSSGLYSLSSVVTVPSSSLGTKTYT CNVDHKPSNTKVDKRVESKYGPPC PPCPAPEFLGGPSVFLFPPKPKDTL MISRTPEVTCVVVDVSQEDPEVQFN WYVDGVEVHNAKTKPREEQFNSTY RVVSVLTVLHQDWLNGKEYKCKVS NKGLPSSIEKTISKAKGQPREPQVYT LPPSQEEMTKNQVSLTCLVKGFYPS DIAVEWESNGQPENNYKTTPPVLDS DGSFFLYSRLTVDKSRWQEGNVFS CSVMHEALHNHYTQKSLSLSLGK |
| TPP-18285 | Cobolimab (TSR-022) | Light Chain | SEQ ID NO: 20 | DIQMTQSPSSLSASVGDRVTITCRA SQSIRRYLNWYHQKPGKAPKLLIYG ASTLQSGVPSRFSGSGSGTDFTLTI SSLQPEDFAVYYCQQSHSAPLTFG GGTKVEIKRTVAAPSVFIFPPSDEQL KSGTASVVCLLNNFYPREAKVQWK VDNALQSGNSQESVTEQDSKDSTY SLSSTLTLSKADYEKHKVYACEVTH QGLSSPVTKSFNRGEC |

Method of Treating Cancer

Within the context of the present invention, the term "cancer" includes, but is not limited to, cancers of the breast, lung, brain, digestive tract, urinary tract, liver, eye, skin, head and neck, thyroid, parathyroid and their distant metastases. Those disorders also include multiple myeloma, lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to lung cancer, particularly small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, melanoma, particularly malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The present invention relates to a method for using the combinations of the present invention, in the treatment or prophylaxis of a cancer, particularly (but not limited to) colorectal cancer, lung cancer, pancreatic cancer, breast cancer, prostate cancer, bladder cancer, gastric cancer, head and neck cancer, liver cancer, brain cancer, melanoma, endometrial cancer, lymphoma, leukemia, etc. Combinations can be utilized to inhibit, block, reduce, decrease, etc., cell proliferation and/or cell division, and/or produce apoptosis, in the treatment or prophylaxis of cancer, in particular (but not limited to) colorectal cancer, lung cancer, breast cancer, prostate cancer, bladder cancer, gastric cancer, head and neck cancer, liver cancer, brain cancer, melanoma, endometrial cancer, lymphoma, leukemia, etc. This method comprises administering to a mammal in need thereof, including a human, an amount of a combination of this invention, or a pharmaceutically acceptable salt, isomer, polymorph, metabolite, hydrate, solvate or ester thereof; etc. which is effective for the treatment or prophylaxis of cancer, in particular (but not limited to) colorectal cancer, lung cancer, pancreatic cancer, breast cancer, prostate cancer, bladder cancer, gastric cancer, head and neck cancer, liver cancer, brain cancer, melanoma, endometrial cancer, lymphoma, leukemia, etc.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

In preferred embodiments, the cancer is lung cancer, in particular non-small cell lung cancer (NSCLC), ovarian cancer, mesothelioma, pancreatic cancer, or gastric cancer, colorectal cancer, head and neck cancer, bladder cancer, bile duct cancer, breast cancer, cervical cancer, esophageal cancer.

Dose and Administration

Based upon standard laboratory techniques known to evaluate compounds useful for the treatment or prophylaxis of cancer, in particular (but not limited to) colorectal cancer, lung cancer, pancreatic cancer, breast cancer, prostate cancer, bladder cancer, gastric cancer, head and neck cancer, liver cancer, brain cancer, melanoma, endometrial cancer, lymphoma, leukemia, etc., by standard toxicity tests and by standard pharmacological assays for the determination of treatment of the conditions identified above in mammals, and by comparison of these results with the results of known medicaments that are used to treat these conditions, the effective dosage of the combinations of this invention can readily be determined for treatment of the indication. The amount of the active ingredient to be administered in the treatment of the condition can vary widely according to such considerations as the particular combination and dosage unit employed, the mode of administration, the period of treatment, the age, weight and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 30 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 2,500 mg of active ingredient, and can be administered one or more times per day or less than once a day. The average dosage for administration by injection, including intravenous, intramuscular, subcutaneous and parenteral injections, and use of infusion techniques will preferably be from 0.01 to 200 mg/kg of total body weight.

Of course the specific initial and continuing dosage regimen for each patient will vary according to the nature and severity of the condition as determined by the attending diagnostician, the activity of the specific combination employed, the age, weight and general condition of the patient, time of administration, route of administration, rate of excretion of the drug, drug combinations, and the like. The desired mode of treatment and number of doses of a Therapies Using Combinations of Component a as Described Supra, Component B as Described Supra, and Component C: One or More Further Pharmaceutical Agents.

The combinations of component A and component B of this invention can be administered as the sole pharmaceutical agent or in combination with one or more further pharmaceutical agents where the resulting combination of components A, B and C causes no unacceptable adverse effects. For example, the combinations of components A and B of this invention can be combined with component C, i.e. one or more further pharmaceutical agents, such as known anti-angiogenesis, anti-hyper-proliferative, anti-inflammatory, analgesic, immunoregulatory, diuretic, anti-arrhytmic, anti-hypercholesterolemia, anti-dyslipidemia, anti-diabetic or antiviral agents, and the like, as well as with admixtures and combinations thereof.

Component C, can be one or more pharmaceutical agents such as 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Generally, the use of component C in combination with a combination of components A and B of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

EXAMPLES

The following examples describe the feasibility of the present invention, but not restricting the invention to these Examples only.

Example 1: Effect of Combination Treatment of TPP-3310 an Antibody Against Human CEACAM6 with Antibodies Directed Against PD-L1 or PD-1 on Activation of PD-1 Positive Virus-Peptide Specific T Cells Since CEACAM6 is not expressed in the rodent (no rodent orthologue) in vivo efficacy studies are not possible and no preclinical in vivo combination studies can be performed to evaluate the therapeutic potential of drug combinations.

Alternatively an in vitro cell assay system was established to test combinations of antibodies against CEACAM6 and PD-1 or PD-L1 for their in vitro efficacy and therapeutic potential.

In this cell assay system PD-1 positive FluM1 virus-peptide specific T cells were used as effector T cells. They were co-cultured with PD-L1 and CEACAM6 positive and FLuM1 peptide loaded cancer cells HCC2935 in the presence of checkpoint inhibitory antibody against CEACAM6, PD-1 or PD-L1 either as single agents or combinations thereof for 24 h-48 h. Induction of proinflammatory cytokines (IFNg) is measured as readout of efficacy.

Antibodies

Antibodies used were TPP-3310 (anti-CEACAM6) which is an huIgG2 antibody against the immune checkpoint molecule CEACAM6 which is overexpressed on cancer cells and myeloid cells, TPP-3615 which is an anti-PD-L1 huIgG2 antibody and which was cloned using the variable domains of Atezolizumab and TPP-2596 which is an anti-PD-1 HuIgG4 Pro antibody which was cloned using the variable domains of Nivolumab. TPP-1238 (huIgG2) and TPP1240 (huIgG4) have been used as isotype control antibodies.

Cell Lines and Culture

HCC2935 cancer cells (ATCC-CRL-2869, lung adenocarcinoma) were cultured in RPMI-1640, 10% FCS, 5% $CO_2$. CEACAM6 and PD-L1 expression was confirmed by FACS analysis. For co-culture assays with virus-peptide specific T cells, the cancer cells were pulsed with a viral FluM1 peptide at 0.2 µg/ml or as indicated.

Generation and Cell Culture of FluM1 Virus-Peptide Specific T Cells

PD-1 expressing virus (influenza)-peptide specific T cells were generated from naïve PBMCs from HLA-A*0201+ healthy donors which were obtained by Ficoll density centrifugation of buffy coats (Deutsches Rotes Kreuz, Mannheim). CD8+ T cells were enriched with MACS negative selection kit (Miltenyi, 130-096-495) according to the manufacturer's protocol. CD8 negative cells were irradiated (35 Gy) and pulsed with 1 µg/ml of the influenza HLA-A*0201 epitope GILGFVFTL (SEQ ID NO: 21) (ProImmune) in X-Vivo-20 medium (Chemically Defined, Serum-free Hematopoietic Cell Medium, Lonza, #BE04-448Q) at 37° C. for 1.5 h and washed thereafter. The cells were re-stimulated with irradiated T2 cells and pulsed with 1 µg/ml of their associated GILGFVFTL (SEQ ID NO: 21) peptide on day 7. On day 14, aliquots were frozen. The samples were thawed and washed immediately before they were used in functional assays. The suitability of the virus-peptide specific T cells was confirmed with tetramer (F391-4A-E, ProImmune) staining and FACS analysis before the co-culture experiments on day 14.

In Vitro Assay: Analysis of Combined Antibody Efficacy in Co-Culture of T Cells and Cancer Cells For the co-culture, cancer cells were detached non-enzymatically with PBS-EDTA for 5-15 min, centrifuged at 1,400 rpm for 5 min, washed and counted. Cancer cells were diluted in X-Vivo-20 (Lonza, #BE04-448Q) at $1 \times 10^5$ cells/ml, pre-treated with TPP-3310, aPD-L1 and/or isotype control antibodies on ice for 10 min. After incubation, 10,000 target cancer cells were seeded in triplicates to 96-well ELISA U-plates.

Virus-peptide specific T cells were harvested, washed with X-Vivo-20, diluted in X-Vivo-20 at $2 \times 10^5$ cells/ml and pre-treated with anti-PD-1 or isotype control antibodies on ice for 10 min. All antibodies were applied at a final concentration of 30 µg/ml. For the combination treatments, TPP-3310 was applied approximately at its half-maximal effective concentration (EC50) of 1 µg/ml to ensure the effects of other antibodies on the activation of T cells. The pre-treated T cells were seeded at 20,000 cells/well onto the target cancer cells.

The co-culture of cancer cells and effector T cells with the antibodies was incubated at 37° C., 5% $CO_2$ for approximately 20 h.

Then supernatants were collected and by centrifuging the co-culture plates at 1,400 rpm for 3 min. The IFN-γ levels in supernatants were measured by ELISA (Human IFN-γ-ELISA Set, BD, #555142) according to the manufacturer's instructions. Optical density of ELISA plates was measured with a Tecan Infinite M200 plate reader.

Data were statistically analyzed with paired or unpaired, two-tailed Student's t-test, using Microsoft Excel 2010 and GraphPad Prism 6. The results with $p<0.05$ were considered significant. Cytokine concentrations were calculated by standard curves. Factors or ratios were calculated by dividing values of TPP-3310 or given combinations by values of the respective isotype controls.

Results

In pre-experiments FLuM1 peptide loaded HCC2935 cancer cells were co-incubated with FluM1 virus-peptide specific T cells. Only in the presence of the cognate virus peptide IFN-γ secretion of the T cells was increased. This increase was dose dependent. IFN-γ secretion ($p<0.05$ to $0.0001$) from the co-culture was further enhanced in the presence of the anti-CEACAM6 antibody TPP-3310, the anti-PD-L1 antibody TPP-3615 or in the presence of the anti-PD-1 antibody TPP-2596. All given as single agents. These data confirmed that the newly established cell assay system consisting of PD-1 positive FluM1 virus-peptide specific T cells and peptide loaded HCC2935 cancer cells is suitable for testing the efficacy of anti-CEACAM6, anti-PD-1 and anti-PD-L1 antibodies in benchmarking and combination experiments.

TABLE 3

Peptide-specificity of virus-peptide specific T cell activation measured by IFNg secretion in co-culture experiments with virus-peptide loaded HCC2935 cancer cells with or without immune checkpoint blocking antibodies against CEACAM6, PD-1 or PD-L1.

| Sample | IFNg [pg/ml] Mean | Standard deviation | Standard error of mean |
|---|---|---|---|
| TC only | 3.5 | 0.5 | 0.3 |
| TC + HCC no peptide | 0.1 | 0.1 | 0.06 |
| TC + HCC/1 µg/ml FLU pep | 792.0 | 29.7 | 17.1 |
| TC + HCC/1 µg/ml FLU pep + 30 µg/ml TPP-1238 | 787.3 | 18.8 | 10.9 |
| TC + HCC/1 µg/ml FLU pep + 30 µg/ml aCEACAM6 (TPP-3310) | 1143.7 | 104.5 | 60.3 |
| TC + HCC/1 µg/ml FLU pep + 30 µg/ml aPD-L1 (TPP-3615) | 887.7 | 35.5 | 20.5 |
| TC + HCC/1 µg/ml FLU pep + 30 µg/ml TPP-1240 | 811.2 | 55.5 | 32.0 |
| TC + HCC/1 µg/ml FLU pep + 30 µg/ml aPD-1 (TPP-2596) | 972.1 | 76.2 | 44.0 |
| TC + HCC/10 µg/ml FLU peptide | 818.8 | 3.5 | 2.0 |
| TC + HCC/1 µg/ml FLU peptide | 915.0 | 29.2 | 16.9 |
| TC + HCC/0.1 µg/ml FLU peptide | 478.1 | 32.9 | 19.0 |
| TC + HCC/0.01 µg/ml FLU peptide | 56.6 | 52.5 | 30.3 |
| TC + HCC/0.001 µg/ml FLU peptide | 5.5 | 0.9 | 0.5 |
| TC + HCC 0.0001 µg/ml FLU peptide | 2.9 | 0.5 | 0.3 |

Description table: Virus-peptide specific T cells (TC) were stimulated with HCC2935 lung cancer cells (HCC) pulsed with serial dilutions of the viral peptide. Antibodies were added at 30 µg/ml. Concentrations of secreted IFN-γ were determined by ELISA. Data are absolute amount of IFN-γ in pg/ml. TPP-3310, aCEACAM6; TPP-3615, aPD-L1; TPP-2596, aPD1; TPP-1238, isotype control for TPP-3310 and TPP3615, aPD-1; TPP-1240, isotype control for TPP-2596.

The effect of the combination of the anti-CEACAM6 antibody TPP-3310 with antibodies directed to PD-L1 was determined overall in 7 independent co-culture experiments (n=7). In the presence of the antibodies we consistently saw an increase of IFNg secretion (absolute mean values) when given as single agents or in combination. In the presence of the PD-L1 antibody total IFNg was increased by 39.6 pg/ml, in the presence of the anti-CEACAM6 antibody TPP-3310 by 196.6 pg/ml and when given in combination by 279.9 pg/ml. This result shows that IFNg secretion is further enhanced upon combination of the PD-L1 antibody with the CEACAM6 antibody and that the effect on IFNg secretion is more than additive.

TABLE 4

Total IFNg secretion in co-culture experiments (n = 7) of FluM1 virus-peptide specific T cells and FluM1 peptide loaded HCC2935 cells in the presence of anti-CEACAM6 and anti-PD-L1 antibody as single agents or in combination

| Antibodies | IFNg [pg/ml] Experiment | | | | | | | Mean | Standard deviation | Standard error of mean |
|---|---|---|---|---|---|---|---|---|---|---|
|  | 1 | 2 | 3 | 4 | 5 | 6 | 7 |  |  |  |
| aPD-L1 (TPP-3615) | 70.7 | 42.0 | 41.9 | 26.3 | 46.8 | 76.1 | −26.3 | 39.6 | 33.9 | 12.8 |
| aCEACAM6 (TPP-3310) | 192.4 | 39.3 | 76.5 | 232.5 | 162.3 | 205.8 | 467.5 | 196.6 | 138.5 | 52.4 |
| aPD-L1 + aCEACAM6 (TPP-3615 + TPP-3310) | 363.8 | 156.0 | 121.9 | 416.7 | 305.5 | 343.0 | 252.5 | 279.9 | 52.4 | 41.3 |

Description table: the HCC2935 lung cancer cells (HCC) were pulsed with the FluM1 peptide at 0.2 µg/ml to stimulate the virus-peptide specific T cells (TC) in the co-culture. Antibodies were applied at 30 µg/ml. For the combination treatments (n = 7), TPP-3310 was added at 1 µg/ml. Concentrations of secreted IFN-γ were determined by ELISA and data are isotype corrected values and are given as pg/ml. TPP-3310, aCEACAM6; TPP-3615, aPD-L1; T-Test of mean values, p-value (<0.05): aPD-L1 vs CEACAM6, p = 0.0439; aPD-L1 vs Combination, p = 0.001; aCEACAM6 vs Combination, p = 0.16

In another study we determined the effect of the combination of the anti-CEACAM6 antibody TPP-3310 with antibodies directed against PD-1 in 7 independent co-culture experiments overall (n=7). In the presence of the antibodies we consistently saw an increase of IFNg secretion (absolute mean values) when given as single agents or in combination.

In the presence of the PD-1 antibody mean total IFNg was increased by 76.1 pg/ml, in the presence of the anti-CEACAM6 antibody TPP-3310 by 166.8 pg/ml and when given in combination by 317.9 pg/ml. This result shows that IFNg secretion is further enhanced upon combination of the PD-1 antibody with the CEACMA6 antibody and that the effect on IFNg secretion is more than additive.

TABLE 5

Total IFNg secretion in co-culture experiments (n = 7) of FluM1 virus-peptide specific T cells and FluM1 peptide loaded HCC2935 cells in the presence of anti-CEACAM6 and anti-PD-1 antibody as single agents or in combination

| | IFNg [pg/ml] | | | | | | | | | |
|---|---|---|---|---|---|---|---|---|---|---|
| | Experiment | | | | | | | | Standard | Standard error of |
| Antibodies | 1 | 2 | 3 | 4 | 5 | 6 | 7 | Mean | deviation | mean |
| aPD-1 (TPP-2596) | 57.9 | 50.2 | 29.9 | 29.3 | 40.5 | 95.5 | 229.1 | 76.1 | 71.2 | 26.9 |
| aCEACAM6 (TPP-3310) | 238.7 | 94.8 | 44.3 | 354.6 | 173.2 | 136.1 | 125.9 | 166.8 | 102.7 | 38.8 |
| aPD-1 + aCEACAM6 (TPP-2596 + TPP-3310) | 388.7 | 195.2 | 88.6 | 495.8 | 343.4 | 326.6 | 386.9 | 317.9 | 135.3 | 51.1 |

Description table: the HCC2935 lung cancer cells (HCC) were pulsed with the FluM1 peptide at 0.2 µg/ml to stimulate the virus-peptide specific T cells (TC) in the co-culture. Antibodies were applied at 30 µg/ml. For the combination treatments (n = 7), TPP-3310 was added at 1 µg/ml. Concentrations of secreted IFN-γ were determined by ELISA and data are isotype corrected values and are given as pg/ml. TPP-3310, aCEACAM6; TPP-2596, aPD-1.
T-Test of mean values, p-value (<0.05): aPD-1 vs CEACAM6, p = 0.13; aPD-L1 vs Combination, p = 0.0034; aCEACAM6 vs Combination, p = 0.0011

Example 2: Effect of Combination Treatment of TPP-3310 an Antibody Against Human CEACAM6 with Antibodies Directed Against TIM-3 on Activation of TIM-3 and PD-1 Positive Virus-Peptide Specific T Cells The combination of anti-CEACAM6 antibody TPP-3310 with an anti-TIM3 antibody was tested as well in the in vitro co-culture assay system with virus-peptide specific T cells and peptide loaded cancer cells In this cell assay system PD1 and TIM3 positive FluM1 virus-antigen specific T cells were used as effector T cells. They were cocultured with PD-L1 and CEACAM6 positive and FLuM1 peptide loaded cancer cells HCC2935 in the presence of checkpoint inhibitory antibody against CEACAM6 and TIM3 either as single agents or combinations thereof for 24 h-48 h. Induction of proinflammatory cytokines (IFNg) was measured as readout of efficacy.

Antibodies

Antibodies used were TPP-3310 (anti-CEACAM6) which is an huIgG2 antibody against the immune checkpoint molecule CEACAM6 which is overexpressed on cancer cells and myeloid cells and MAB2365 (rIgG2, R&D Jackson immunoresearch) which is an anti-TIM3 Antibody. TPP-1238 (huIgG2) and MAB006 (rIgG2; R&D). have been used as isotype control antibodies.

Cell Lines and Culture

HCC2935 cancer cells (ATCC-CRL-2869, lung adenocarcinoma) were cultured in RPMI-1640, 10% FCS, 5% $CO_2$. CEACAM6 and PD-L1 and TIM-3 expression was confirmed by FACS analysis. For co-culture assays with virus-peptide specific T cells, the cancer cells were pulsed with a viral FluM1 peptide at 0.2 µg/ml or as indicated.

Generation and Cell Culture of FluM1 Virus-Peptide Specific T Cells

PD-1 expressing virus (influenza)-peptide specific T cells were generated from naïve PBMCs from HLA-A*0201+ healthy donors which were obtained by Ficoll density centrifugation of buffy coats (Deutsches Rotes Kreuz, Mannheim). CD8+ T cells were enriched with MACS negative selection kit (Miltenyi, 130-096-495) according to the manufacturer's protocol. CD8 negative cells were irradiated (35 Gy) and pulsed with 1 µg/ml of the influenza HLA-A*0201 epitope GILGFVFTL (SEQ ID NO: 21) (ProImmune) in X-Vivo-20 medium (Chemically Defined, Serum-free Hematopoietic Cell Medium, Lonza, #BE04-448Q) at 37° C. for 1.5 h and washed thereafter. The cells were re-stimulated with irradiated T2 cells and pulsed with 1 µg/ml of their associated GILGFVFTL (SEQ ID NO: 21) peptide on day 7. On day 14, aliquots were frozen. The samples were thawed and washed immediately before they were used in functional assays. The suitability of the virus-peptide specific T cells was confirmed with tetramer (F391-4A-E, ProImmune) staining and FACS analysis before the co-culture experiments on day 14.

In Vitro Assay: Analysis of Combined Antibody Efficacy in Coculture of T Cells and Cancer Cells For the co-culture, cancer cells were detached non-enzymatically with PBS-EDTA for 5-15 min, centrifuged at 1,400 rpm for 5 min, washed and counted. Cancer cells were diluted in X-Vivo-20 (Lonza, #BE04-448Q) at $1\times10^5$ cells/ml, pre-treated with TPP-3310 and/or isotype control antibodies on ice for 10 min. After incubation, 10,000 target cancer cells were seeded in triplicates to 96-well ELISA U-plates.

Virus-peptide specific T cells were harvested, washed with X-Vivo-20, diluted in X-Vivo-20 at $2\times10^5$ cells/ml and pre-treated with anti-TIM3 or isotype control antibodies on ice for 10 min. All antibodies were applied at a final concentration of 30 µg/ml., except the anti-TIM3 antibody which was used at 50 µg/ml. For the combination treatments, TPP-3310 was applied approximately at its half-maximal effective concentration (EC50) of 1 µg/ml to ensure the effects of other antibodies on the activation of T cells. The pre-treated T cells were seeded at 20,000 cells/well onto the target cancer cells.

The co-culture of cancer cells and effector T cells with the antibodies was incubated at 37° C., 5% $CO_2$ for approximately 20 h.

Then supernatants were collected by centrifuging the co-culture plates at 1,400 rpm for 3 min. The IFN-γ levels in supernatants were measured by ELISA (Human IFN-γ-ELISA Set, BD, #555142) according to the manufacturer's instructions. Optical density of ELISA plates was measured with a Tecan Infinite M200 plate reader.

Data were statistically analyzed with paired or unpaired, two-tailed Student's t-test, using Microsoft Excel 2010 and GraphPad Prism 6. The results with p<0.05 were considered significant. Cytokine concentrations were calculated by standard curves. Factors or ratios were calculated by dividing values of TPP-3310 or given combinations by values of the respective isotype controls.

Results

In pre-experiments FLuM1 peptide loaded HCC2935 cancer cells were co-incubated with FluM1 virus-peptide specific T cells. Only in the presence of the cognate virus peptide IFN-γ secretion of the T cells was increased. This increase was dose dependent. IFN-γ secretion ($p<0.05$ to 0.0001) from the co-culture was further enhanced in the presence of the anti-CEACAM6 antibody TPP-3310 or in the presence of the anti-TIM3 antibody MAB2365. All were given as single agents. These data confirmed that the newly established cell assay system consisting of TIM-3 and PD-1 positive FluM1 virus-specific T cells and peptide loaded HCC2935 cells is suitable for testing the efficacy of anti-CEACAM6 and anti-TIM3 mAbs in benchmarking and combination experiments.

TABLE 6

Peptide-specificity of virus-specific T cell activation measured by IFNg secretion in co-culture experiments with virus peptide loaded HCC2935 with or without immune checkpoint blocking antibodies against CEACAM6 and TIM3.

| Sample | Mean | Standard deviation | Standard error of mean |
|---|---|---|---|
| TC only | 0 | 0 | 0 |
| TC + HCC no peptide | 0 | 0 | 0 |
| TC + HCC + 0.5 µg/ml FLU pep | 778.4 | 34.0 | 19.7 |
| TC + HCC + 0.5 µg/ml FLU pep + 30 µg/ml aCEACAM6 (TPP-3310) | 1131.1 | 26.2 | 15.1 |
| TC + HCC + 0.5 µg/ml FLU pep + 50 µg/ml aTIM-3 (MAB2365) | 925.3 | 46.2 | 26.7 |

TABLE 6-continued

Peptide-specificity of virus-specific T cell activation measured by IFNg secretion in co-culture experiments with virus peptide loaded HCC2935 with or without immune checkpoint blocking antibodies against CEACAM6 and TIM3.

| Sample | Mean | Standard deviation | Standard error of mean |
|---|---|---|---|
| TC + HCC + 0.5 µg/ml FLU pep + 50 µg/ml Isotype (Mab006) | 735.0 | 11.8 | 6.8 |
| TC + HCC 10 µg/ml FLU peptide | 843.0 | 17.7 | 10.2 |
| TC + HCC 1 µg/ml FLU peptide | 804.3 | 50 | 28.9 |
| TC + HCC 0.1 µg/ml FLU peptide | 359.9 | 3.8 | 2.2 |
| TC + HCC 0.01 µg/ml FLU peptide | 49.7 | 46.5 | 26.8 |
| TC + HCC 0.001 µg/ml FLU peptide | 0 | 0 | 0 |
| TC + HCC 0.0001 µg/ml FLU peptide | 0 | 0 | 0 |

Description table: Virus-specific T cells (TC) were stimulated with HCC2935 lung cancer cells (HCC) pulsed with serial dilutions of the viral peptide. Antibodies were added at 30 µg/ml except the anti-TIM3 mAb which was used at 50 µg/ml. Concentrations of secreted IFN-γ were determined by ELISA. Data are absolut amount of IFN-γ in pg/ml. TPP-3310, aCEACAM6; MAB2365, aTIM3; TPP-1238, huIgG2 isotype control;. MAB006, rIgG2 isotype control.

The effect of the combination of the anti-CEACAM6 antibody TPP-3310 with the anti-TIM3 Mab 2365 was determined overall in 7 independent co-culture experiments (n=7). In the presence of the antibodies we consistently saw an increase of IFNg secretion (absolute mean values) when given as single agents or in combination. In the presence of the TIM-3 antibody total IFNg was increased by 181.5 pg/ml, in the presence of the anti-CEACAM6 antibody TPP-3310 by 228.0 pg/ml and when given in combination by 562.6 pg/ml. This result shows that IFNg secretion is further strongly enhanced upon combination of the TIM-3 antibody with the CEACAM6 antibody and that the effect on IFNg secretion is more than additive. It also shows activity in the presence of an active PD-L1/PD-1 axis and effects are stronger compared to the previous examples.

TABLE 7

Total IFNg secretion in co-culture experiments (n = 7) of FluM1 virus-peptide specific T cells and FluM1 peptide loaded HCC2935 cells in the presence of anti-CEACAM6 TPP-3310 and anti-TIM-3 antibody MAB2365 as single agents or in combination.

| | IFNg [pg/ml] | | | | | | | | | |
|---|---|---|---|---|---|---|---|---|---|---|
| | Experiment | | | | | | | | Standard | Standard error of |
| Antibodies | 1 | 2 | 3 | 4 | 5 | 6 | 7 | Mean | deviation | mean |
| aTIM3 (MAB2365)- | 65. | 67.7 | 37.0 | 246.6 | 287.1 | 288.2 | 277.7 | 181.5 | 117.7 | 44.5 |
| aCEACAM6 (TPP-3310) | 233.0 | 159.3 | 33.3 | 402.9 | 217.0 | 242.4 | 307.3 | 228.0 | 115.3 | 43.6 |
| aTIM3 + aCEACAM6 (MAB2365 + TPP-3310) | 544.7 | 212.3 | 141.8 | 1136.7 | 753.0 | 758.2 | 391.5 | 562.6 | 349.6 | 132.1 |

Description table: HCC2935 lung cancer cells (HCC) were pulsed with the FluM1 peptide at 0.2 µg/ml to stimulate the virus-peptide specific T cells (TC) in the co-culture. TIM3 antibody was applied at 50 µg/ml. For the combination treatments (n = 7), TPP-3310 was added at 1 µg/ml. Concentrations of secreted IFN-γ were determined by ELISA. Data are isotype corrected values and are given as pg/ml. TPP-3310, aCEACAM6; .MAB2365, aTIM3

T-Test of mean values, p-value (<0.05): a-TIM3 vs CEACAM6, p = 0.24; a-TIM3 vs Combination, p = 0.01; aCEACAM6 vs Combination, p = 0.016

Example 3: Effect of Combination Treatment of TPP-3310 an Antibody Against Human CEACAM6 with Antibodies Directed Against TIM-3 on Activation of Survivin-Peptide Specific T Cells Previously TPP-3310 was found to increase IFN-γ secretion by survivin-peptide specific T cells in co-cultures with breast, colorectal and lung cancer cells. In another example the combination of anti-CEACAM6 antibody TPP-3310 with an anti-TIM3 antibody MAB2365 (R&D Jackson Immunoresearch) was tested in co-cultures of survivin-peptide specific T cells as alternative T cell source with HCC2935 lung cancer or KS breast cancer cells.

Antibodies

Antibodies used were TPP-3310 (anti-CEACAM6) which is an huIgG2 antibody against the immune checkpoint molecule CEACAM6 which is overexpressed on cancer cells and myeloid cells. MAB2365 (rIgG2, R&D Jackson Immunoresearch) which is an anti-TIM3 antibody. TPP-1238 (huIgG2) and MAB006 (rIgG2; R&D Jackson Immunoresearch) have been used as isotype control antibodies.

Cell Lines and Culture

HCC2935 cancer cells (ATCC-CRL-2869, lung adenocarcinoma) were cultured in RPMI-1640, 10% FCS, 5% $CO_2$. KS breast cancer cells were cultured in DMEM, 10% FCS. CEACAM6 and PD-L1 expression was confirmed by FACS analysis.

Generation and Cell Culture of Survivin Specific T Cells:

The tumor antigen-specific (i.e. survivin-peptide specific) T cells were generated from peripheral blood mononuclear cells (PBMCs) of healthy donors as described in the literature (Moosmann A. Gezielte Reaktivierung spezifischer zytotoxischer T-Zellen mit Epstein-Barr-Virus-Vektoren. Dissertation, Ludwig-Maximilians-University Munich, Germany. 2002; Brackertz B, Conrad H, Daniel J, Kast B, Krönig H, Busch D H, et al. FLT3-regulated antigens as targets for leukemia-reactive cytotoxic T lymphocytes. Blood Cancer Journal. 2011; 1(3): e11.)

In Vitro Assay: Analysis of Combined Antibody Efficacy in Co-Culture of T Cells and Cancer Cells For the co-culture, cancer cells were detached non-enzymatically with PBS-EDTA for 5-15 min, centrifuged at 1,400 rpm for 5 min, washed and counted. Cancer cells were diluted in X-Vivo-20 (Lonza, #BE04-448Q) at $1 \times 10^5$ cells/ml, pre-treated with TPP-3310 and/or isotype control antibodies on ice for 10 min. After incubation, 10,000 target cancer cells were seeded in triplicates to 96-well ELISA U-plates.

Survivin-peptide specific T cells were harvested, washed with X-Vivo-20, diluted in X-Vivo-20 at $2 \times 10^5$ cells/ml and pre-treated with anti-TIM-3 MAB2365 or isotype control antibodies on ice for 10 min. The Anti-TIM-3 antibody was applied at a final concentration of 50 μg/ml. For the combination treatments, TPP-3310 was applied approximately at its half-maximal effective concentration (EC50) of 1 μg/ml to ensure effects of other antibodies on the activation of T cells. The pre-treated T cells were seeded at 20,000 cells/well onto the target cancer cells. The co-culture of cancer cells and effector T cells with the antibodies was incubated at 37 C, 5% CO2 for approximately 20 h. Then supernatants were collected by centrifuging the co-culture plates at 1,400 rpm for 3 min. The IFN-γ levels in supernatants were measured by ELISA (Human IFN-γ-ELISA Set, BD, #555142) according to the manufacturer's instructions. Optical density of ELISA plates was measured with a Tecan Infinite M200 plate reader.

Data were statistically analyzed with paired or unpaired, two-tailed Student's t-test, using Microsoft Excel 2010 and GraphPad Prism 6. The results with p<0.05 were considered significant. Cytokine concentrations were calculated by standard curves. Factors or ratios were calculated by dividing values of TPP-3310 or given combinations by values of the respective isotype controls.

TABLE 8

Total IFNg secretion in co-culture experiments (n = 1) of survivin-peptide specific T cells and HCC2935 lung cells (HCC) in the presence of anti-CEACAM6 TPP-3310 and anti-TIM-3 MAB2365 antibody administered as single agents or in combination.

| | IFNg [pg/ml] | |
|---|---|---|
| Antibodies | Mean* IFNg (pg/ml) | Standard deviation** IFNg (pg/ml) |
| aTIM-3 (MAB2365) | 63.6 | −0.4 |
| aCEACAM6 (TPP-3310) | 343.1 | 18.3 |
| aTIM3 + aCEACAM6 (MAB2365 + TPP-3310) | 722.7 | 31.7 |

Description table: The anti-TIM-3 antibody MAB2365 was applied at 50 μg/ml. For combination treatments (n = 1), TPP-3310 was added at 1 μg/ml. Concentrations of secreted IFN-γ were determined by ELISA. Data are isotype corrected values and are given as pg/ml. TPP-3310, aCEACAM6, MAB2365, aTIM3
*Mean value of triplicate, isotype corrected
**Standard deviation calculated from triplicate values with Excel software

TABLE 9

Total IFNg secretion in coculture experiments (n = 1) of survivin-peptide specific T cells and KS breast cancer cells in the presence of anti-CEACAM6 antibody TPP-3310 and anti-TIM-3 antibody MAB2365 administered as single agents or in combination.

| | IFNg [pg/ml] | |
|---|---|---|
| Antibodies | Mean* IFNg (pg/ml) | Standard deviation** IFNg (pg/ml) |
| aTIM3 (MAB2365) | 18.3 | −2.8 |
| aCEACAM6 (TPP-3310) | 38.4 | 6.2 |
| aTIM3 + aCEACAM6 (MAB2365 + TPP-3310) | 77.5 | 6.5 |

Description table: The TIM3 antibody MAB2365 was applied at 50 μg/ml. For combination treatments (n = 1), TPP-3310 was added at 1 μg/ml. Concentrations of secreted IFN-γ were determined by ELISA. Data are isotype corrected values and are given as pg/ml. TPP-3310, aCEACAM6; MAB2365, aTIM3
*Mean value of triplicate, isotype corrected
**Standard deviation calculated from triplicate values with Excel software As single agents, TPP-3310 and the anti-TIM-3 MAB2365 antibody increased IFN-γ secretion of survivin-peptide specific T cells by 343.1 pg/ml and by 63.6 pg/ml respectively in co-cultures with HCC2935 cell line and 38.4 pg/ml and 18.3 pg/ml in co-culture with the KS cell line.

When combined, TPP-3310 and the anti-TIM3 antibody MAB2365 increased IFN-γ secretion by 722.7 pg/ml on HCC2935 cells and by 77.5 pg/ml on KS cells. This result shows that IFNg secretion is further enhanced upon combination of the TIM-3 antibody with the CEACAM6 antibody and that the effect on IFNg secretion is clearly more than additive.

The invention claimed is:

1. A method of treating cancer comprising administering anti-CEACAM6 antibody before, after or with an effective amount of an anti-TIM-3 antibody in the treatment of cancer, wherein the cancer to be treated expresses CEACAM6, wherein the anti-CEACAM6 antibody comprises H-CDR1 comprising the amino acid sequence of SEQ ID NO: 2, H-CDR2 comprising the amino acid sequence of SEQ ID NO: 3, H-CDR3 comprising the amino acid sequence of SEQ ID NO: 4, L-CDR1 comprising the amino acid sequence of SEQ ID NO: 6, L-CDR2 comprising the amino acid sequence of SEQ ID NO: 7, and L-CDR3 comprising the amino acid sequence of SEQ ID NO: 8.

2. The method of claim 1, wherein the anti-CEACAM6 antibody comprises a variable heavy chain sequence of SEQ ID NO:1 and a variable light chain sequence of SEQ ID NO:5.

3. The method of claim 1, wherein the anti-CEACAM6 antibody comprises a heavy chain region of SEQ ID NO: 9 and a light chain region of SEQ ID NO: 10.

4. The method of claim 1, wherein the anti-TIM-3 antibody is cobolimab, MBG-453, BMS-986258, Sym-023, LY-3321367 or INCAGN-2390.

5. The method of claim 1, wherein the anti-TIM-3 antibody comprises H-CDR1 comprising the amino acid sequence of SEQ ID NO: 12, H-CDR2 comprising the amino acid sequence of SEQ ID NO: 13, H-CDR3 comprising the amino acid sequence of SEQ ID NO: 14, L-CDR1 comprising the amino acid sequence of SEQ ID NO: 16, L-CDR2 comprising the amino acid sequence of SEQ ID NO: 17, and L-CDR3 comprising the amino acid sequence of SEQ ID NO: 18.

6. The method of claim 1, wherein the anti-TIM-3 antibody comprises a variable heavy chain sequence (VH) of SEQ ID NO:11 and a variable light chain sequences (VL) of SEQ ID NO:15.

7. The method of claim 1, wherein the anti-TIM-3 antibody comprises a heavy chain region (HC) of SEQ ID NO: 19 and a light chain region (LC) of SEQ ID NO: 20.

8. The method of claim 1, wherein the cancer is lung cancer, ovarian cancer, mesothelioma, pancreatic cancer, gastric cancer, colorectal cancer, head and neck cancer, bladder cancer, bile duct cancer, breast cancer, cervical cancer, or esophageal cancer.

9. The method of claim 8, wherein the lung cancer is non-small cell lung cancer.

10. The method of claim 1, wherein at least one of the anti-CEACAM6 antibody or an anti-TIM-3 antibody is administered in simultaneous, separate, or sequential combination with one or more pharmaceutical agents.

11. The method of claim 1, wherein the anti-CEACAM6 antibody is in admixture with the anti-TIM-3 antibody.

\* \* \* \* \*